United States Patent [19]

Bushnell et al.

[11] Patent Number: 5,286,894

[45] Date of Patent: Feb. 15, 1994

[54] FUNGICIDES

[75] Inventors: Michael J. Bushnell; Kevin Beautement, both of Wokingham; John M. Clough, High Wycombe; Vivienne M. Anthony, Upminster; Paul deFraine, Wokingham; Christopher Godfrey, Bracknell, all of England

[73] Assignee: Imperial Chemical Industries PLC, London, England

[21] Appl. No.: 907,573

[22] Filed: Jul. 2, 1992

Related U.S. Application Data

[63] Continuation of Ser. No. 786,803, Oct. 11, 1985.

[30] Foreign Application Priority Data

| Oct. 19, 1984 | [GB] | United Kingdom | 8426473 |
| Dec. 20, 1984 | [GB] | United Kingdom | 8432265 |
| May 23, 1985 | [GB] | United Kingdom | 8513104 |
| May 23, 1985 | [GB] | United Kingdom | 8513115 |

[51] Int. Cl.$^5$ .............................................. C07C 69/76
[52] U.S. Cl. ......................................... 560/55; 560/104
[58] Field of Search .......................... 560/104, 106, 55

[56] References Cited

U.S. PATENT DOCUMENTS

| 4,709,078 | 11/1987 | Schirmer et al. | 560/60 |
| 4,723,034 | 2/1988 | Schirmer et al. | 560/60 |

FOREIGN PATENT DOCUMENTS

| 0015502 | 9/1980 | European Pat. Off. |
| 1301817 | 1/1973 | United Kingdom |

OTHER PUBLICATIONS

Thesis by George Schramm entitled "Novel Antibiotics from Higher Fung", with partial English translation.
CA 98(26):221538g (1983).
CA 99(15):115553u (1983)
CA 87(23):177461y (1977).
CA 91(9):74390c (1979)
CA 101(21):191358j (1984).
CA 75(5):35079h (1970)
CA 83(23):192956z (1975).
CA 96(11):85178u (1981).
CA 102(3):24339t (1984).
CA 75(25):15165d (1971)
CA 77(7):47849g (1972).
CA 96(21):180903k (1982)
CA 85 (3):20786u (1976).
CA 88(25):189306k (1978)
CA 96(21):180903k (1982).
CA 67(19):90756m (1966)
CA 95(8):63659d (1981).
CA 88(23):170112x (1977)
CA 101(23):21165z (1981).
CA 88(25):189306k (1978).

*Primary Examiner*—Paul J. Killos
*Attorney, Agent, or Firm*—Cushman, Darby & Cushman

[57] ABSTRACT

This invention relates to derivatives of acrylic acid useful as fungicides, to processes for preparing them, to fungicidal compositions containing them, and to methods of combating fungi, especially fungal infections in plants, using them.

1 Claim, No Drawings

FUNGICIDES

This is a continuation of application No. 06,786,803, filed Oct. 11, 1985.

The invention provides a compound having the general formula (I):

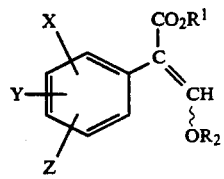

and stereoisomers thereof, wherein X, Y and Z, which may be the same or different, are hydrogen or halogen atoms, or optionally substituted alkyl, optionally substituted alkenyl, optionally substituted aryl, optionally substituted alkynyl, haloalkyl, alkoxy, haloalkoxy, optionally substituted aryloxy, optionally substituted arylalkoxy, optionally substituted acyloxy, optionally substituted amino, optionally substituted arylazo, acylamino, nitro, nitrile, —$CO_2R^3$, —$CONR^4R^5$, —$COR^6$, —$CR^7$=$NR^8$, or —$N$=$CR^9R^{10}$ groups or the groups X and Y, when they are in adjacent positions on the phenyl ring, may join to form a fused ring, either aromatic or aliphatic, optionally containing one or more heteroatoms; and $R^1$, $R^2$, $R^3$, $R^4$, $R^5$, $R^6$, $R^7$, $R^8$, $R^9$ and $R^{10}$, which may be the same or different, are hydrogen atoms or alkyl, cycloalkyl, alkenyl, alkynyl, optionally substituted aryl, optionally substituted aralkyl, or cycloalkylalkyl groups; and metal complexes thereof.

The compounds of the invention contain at least one carbon-carbon double bond, and are sometimes obtained in the form of mixtures of geometric isomers. However, these mixtures can be separated into individual isomers, and this invention embraces such isomers.

Alkyl groups can be in the form of straight or branched chains, and preferably contain 1 to 6 carbon atoms; examples are methyl, ethyl, propyl, (n- or iso-propyl) and butyl (n-, sec-, iso- or t-butyl). The methyl group is the preferred alkyl group for both $R^1$ and $R^2$.

In a further aspect the invention provides compounds having the general formula (I):

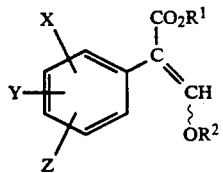

and stereoisomers thereof, wherein X, Y and Z, which may be the same or different, are hydrogen or halogen atoms, or optionally substituted alkyl, optionally substituted alkenyl, optionally substituted aryl, optionally substituted alkynyl, haloalkyl, alkoxy, haloalkoxy, optionally substituted aryloxy, optionally substituted arylalkoxy, amino, acylamino, nitro, nitrile, —$CO_2R^3$, —$CONR^4R^5$, or —$COR^6$, groups; and $R^1$, $R^2$, $R^3$, $R^4$, $R^5$, and $R^6$, which may be the same or different, are hydrogen atoms or alkyl, cycloalkyl, alkenyl, alkynyl, optionally substituted aryl, optionally substituted aralkyl, or cycloalkylalkyl groups; and metal complexes thereof.

In another aspect the invention provides compounds having the general formula (I):

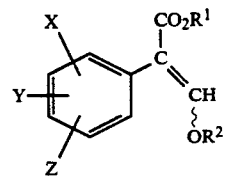

and stereoisomers thereof, wherein X, Y and Z, which may be the same or different, are hydrogen or halogen atoms, or optionally substituted alkyl, optionally substituted alkenyl, optionally substituted aryl, optionally substituted alkynyl, haloalkyl, alkoxy, optionally substituted aryloxy, optionally substituted arylalkoxy, optionally substituted amino, —$CO_2R^3$, —$COR^6$, groups, or the groups X and Y, when they are in adjacent positions on the phenyl ring, may join to form a fused aromatic ring; and $R^1$, $R^2$, $R^3$, and $R^6$, which may be the same or different, are alkyl, optionally substituted phenyl, or optionally substituted aralkyl groups.

In a still further aspect the invention provides compounds having the general formula (I):

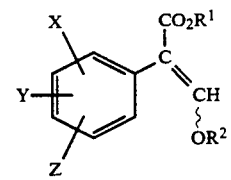

and stereoisomers thereof, wherein X, Y and Z, which may be the same or different, are hydrogen, fluorine, chlorine or bromine atoms, or $C_{1-4}$ alkyl, $C_{2-5}$ alkenyl, $C_{2-5}$ alkynyl, phenyl, $C_{1-4}$ haloalkyl, $C_{1-4}$ alkoxy, phenoxy, benzyloxy or mono- or dialkylamino groups, or the groups X and Y, when they are in adjacent positions on the phenyl ring, join to form a fused aromatic ring, the aliphatic moieties of any of the foregoing being optionally substituted with one or more $C_{1-4}$ alkoxy groups, fluorine, chlorine or bromine atoms, phenyl rings which themselves are optionally substituted, heterocyclic rings which are either aromatic or non-aromatic and are themselves optionally substituted, nitro, amino, nitrile, hydroxyl or carboxyl groups; and wherein the phenyl moieties of any of the foregoing are optionally substituted with one or more fluorine, chlorine or bromine atoms, phenyl rings, $C_{1-4}$ alkyl, $C_{1-4}$ alkoxy; nitro, amino, nitrile, hydroxyl or carboxyl groups; ad $R^1$ and $R^2$, which may be the same or different, are $C_{1-4}$ alkyl, phenyl or benzyl groups, each optionally substituted with halogen atoms.

In yet another aspect the invention provides compounds having the general formula (XI):

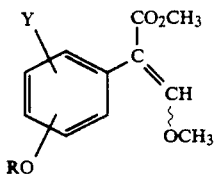

wherein R is an optionally substituted phenyl or an optionally substituted benzyl group, and Y is a hydrogen or a halogen (fluorine, chlorine or bromine) atom or a methyl, methoxyl, nitrol, nitrile, carboxyl or methoxycarbonyl group.

In another aspect the invention provides compounds having the general formula (XII):

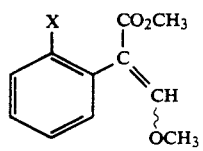

and stereoisomers thereof, wherein X is an alkyl, alkenyl, alkynyl, aryloxy or arylalkoxy group, each of which is optionally substituted.

In a further aspect the invention provides compounds having the general formula (XIII):

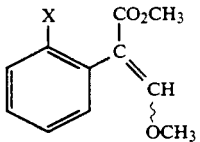

and stereoisomers thereof, wherein X is an optionally substituted alkyl, optionally substituted alkenyl, or optionally substituted alkynyl group.

In particular the invention, in a still further aspect, provides compounds wherein the optional substituents in the foregoing paragraph are phenyl, itself optionally substituted with one or more of the following: fluorine, chlorine, bromine, $C_{1-4}$ alkyl (especially methyl), $C_{1-4}$ alkoxy (especially methoxy), or nitro.

In a still further aspect the invention provides compounds having the general formula (XIV):

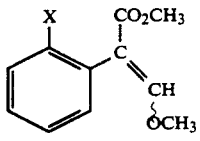

and stereoisomers thereof, wherein X is an optionally substituted aryloxy group or an optionally substituted arylalkoxy group.

In the foregoing paragraph X can be phenoxy or benzyloxy, either of which can be optionally substituted with one or more halogens (fluorine, chlorine or bromine) or a methyl, methoxyl, ethyl, ethoxyl, nitro, nitrile, carboxyl or methoxycarbonyl group.

In a yet further aspect the invention provides compounds having the general formula (XV):

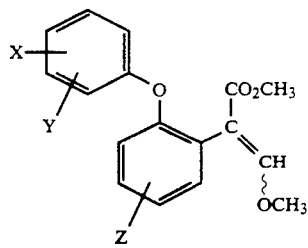

and stereoisomers thereof, wherein X, Y and Z, which may be the same or different, are fluorine, chlorine, bromine, or hydrogen atoms, or methyl, methoxyl or nitro groups.

The invention provides the compounds:

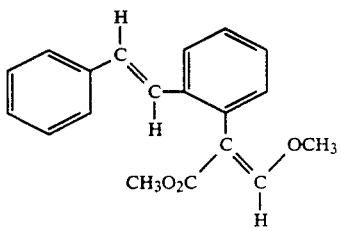

(compound number 9 of Table I below).

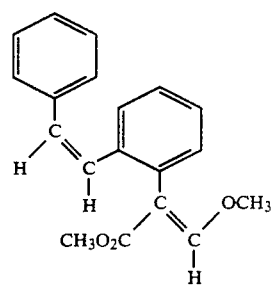

(Compound number 13 of Table I below).

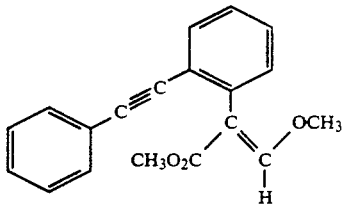

(Compound number 19 of table I below).

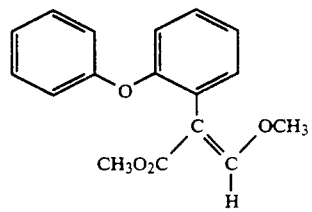

(Compound number 1 of Table II below).

TABLE I (Compound number 1 of Table IV below).

| Compound No. | $R^1$ | $R^2$ | X | Y | Z | Melting point (°C.) | olefinic* | isomer+ |
|---|---|---|---|---|---|---|---|---|
| 1 | $CH_3$ | $CH_3$ | H | H | H | 37-38 | 7.55 | E |
| 2 | $CH_3$ | $CH_3$ | H | H | H | oil | 6.65 | Z |
| 3 | $CH_3CH_2$ | $CH_3$ | H | H | H | oil | 7.53 | E |
| 4 | $CH_3$ | $CH_3CH_2$ | H | H | H | oil | 7.62 | E |
| 5 | $CH_3CH_2$ | $CH_3CH_2$ | H | H | H | oil | 7.62 | E |
| 6 | $C_6H_5CH_2$ | $CH_3$ | H | H | H | oil | 7.56 | E |
| 7 | $CH_3$ | $C_6H_5CH_2$ | H | H | H | 37-38 | 7.67 | E |
| 8 | $(CH_3)_3C$ | $CH_3$ | H | H | H | oil | 7.44 | E |
| 9 | $CH_3$ | $CH_3$ | 2-(E—$C_6H_5$CH:CH) | H | H | 107-108 | 7.63 | E |
| 10 | $CH_3$ | $CH_3$ | 2-(E—$C_6H_5$CH:CH) | H | H | oil | 6.57 | Z |
| 11 | $CH_3$ | $CH_3$ | 3-(E—$C_6H_5$CH:CH) | H | H | 104-105 | 7.58 | E |
| 12 | $CH_3$ | $CH_3$ | 4-(E—$C_6H_5$CH:CH) | H | H | 75-76 | 7.56 | E |
| 13 | $CH_3$ | $CH_3$ | 2-(Z—$C_6H_5$CH:CH) | H | H | oil | 7.50 | E |
| 14 | $CH_3$ | $CH_3$ | 2-(Z—$C_6H_5$CH:CH) | H | H | 93-94 | 6.34 | Z |
| 15 | $(CH_3)_3C$ | $CH_3$ | 2-(Z—$C_6H_5$CH:CH) | H | H | oil | 7.37 | E |
| 16 | $CH_3$ | $(CH_3)_3C$ | 2-(Z—$C_6H_5$CH:CH) | H | H | oil | 7.87 | E |
| 17 | $CH_3$ | $CH_3$ | 2-$C_6H_5CH_2CH(CH_3)$ | H | H | | | E |
| 18 | $CH_3$ | $CH_3$ | 2-$C_6H_5CH_2C(CH_3)_2$ | H | H | | | E |
| 19 | $CH_3$ | $CH_3$ | 2-$C_6H_5$C:C | H | H | 86-87 | 7.58 | E |
| 20 | $CH_3$ | $CH_3$ | 2-$CH_2$:CH | H | H | oil | 7.57 | E |
| 21 | $CH_3$ | $CH_3$ | 2-Cl | H | H | 65-66 | 7.60 | E |
| 22 | $CH_3$ | $CH_3$ | 4-Cl | H | H | 61-62 | 7.56 | E |
| 23 | $CH_3$ | $CH_3$ | 2-Cl | 4-Cl | H | 68-69 | 7.56 | E |
| 24 | $CH_3$ | $CH_3$ | 2-Cl | 6-Cl | H | 141-142 | 7.61 | E |
| 25 | $CH_3$ | $CH_3$ | 3-Cl | 5-Cl | H | 126-127 | 7.58 | E |
| 26 | $CH_3$ | $CH_3$ | 3-Cl | 5-Cl | H | oil | 6.70 | Z |
| 27 | $CH_3$ | $CH_3$ | 2-Cl | 6-F | H | 79-80 | 7.62 | E |
| 28 | $CH_3$ | $CH_3$ | 2-$CH_3$ | H | H | oil | 7.55 | E |
| 29 | $CH_3$ | $CH_3$ | 2-$CH_3$ | H | H | 62-63 | 6.52 | Z |
| 30 | $CH_3$ | $CH_3$ | 2-($CO_2CH_3$) | H | H | oil | 7.52 | E |
| 31 | $CH_3$ | $CH_3$ | 2-$CF_3$ | H | H | 65-66 | 7.56 | E |
| 32 | $CH_3$ | $CH_3$ | 2-$C_6H_5$ | H | H | 106-107 | 7.34 | E |
| 33 | $CH_3$ | $CH_3$ | 2-$C_6H_5N(CH_3)CO$ | H | H | | | |
| 34 | $CH_3$ | $CH_3$ | 2-$C_6H_5CON(CH_3)$ | H | H | | | |
| 35 | $CH_3$ | $CH_3$ | 2-$C_6H_5CO$ | H | H | 82-85 | 7.30 | E |
| 36 | $CH_3$ | $CH_3$ | 2-$C_6H_5CO_2$ | H | H | | | E |
| 37 | $CH_3$ | $CH_3$ | 2-$C_6H_5O_2C$ | H | H | | | E |
| 38 | $CH_3$ | $CH_3$ | 2-$(CH_3)_3CO_2C$ | H | H | | | E |
| 39 | $CH_3$ | $CH_3$ | 2-(cyclohexyl)$O_2C$ | H | H | | | E |
| 40 | $CH_3$ | $CH_3$ | 2-$C_6H_5CH_2$ | H | H | oil | 7.48 | E |
| 41 | $CH_3$ | $CH_3$ | 2-(4-Cl—$C_6H_4$)$CH_2$ | H | H | | | E |
| 42 | $CH_3$ | $CH_3$ | 2-(4-$CH_3O$—$C_6H_4$)$CH_2$ | H | H | oil | 7.50 | E |
| 43 | $CH_3$ | $CH_3$ | 2-$C_6H_5(CH_3)_2C$ | H | H | | | E |
| 44 | $CH_3$ | $CH_3$ | 2-$C_6H_5CH(OH)$ | H | H | | | E |
| 45 | $CH_3$ | $CH_3$ | 2-$NO_2$ | H | H | oil | under aromatics | E |
| 46 | $CH_3$ | $CH_3$ | 2-$NH_2$ | H | H | | | E |
| 47 | $CH_3$ | $CH_3$ | 2-$C_6H_5$N:N | H | H | | | E |
| 48 | $CH_3$ | $CH_3$ | 2-(4-$(CH_3)_2$N—$C_6H_4$N:N) | H | H | | | E |
| 49 | $CH_3$ | $CH_3$ | 2-(4-$CH_3O$—$C_6H_4$N:N) | H | H | | | E |
| 50 | $CH_3$ | $CH_3$ | 2-$CH_3O_2CCH_2CH_2$ | H | H | | | E |
| 51 | $CH_3$ | $CH_3$ | 2-$(CH_3)_2CH$ | H | H | | | E |
| 52 | $CH_3$ | $CH_3$ | 2-$C_6H_5S$ | H | H | oil | 7.51 | E |
| 53 | $CH_3$ | $CH_3$ | 2-$C_6H_5S(O)$ | H | H | oil | under aromatics | E |
| 54 | $CH_3$ | $CH_3$ | 2-$C_6H_5S(O)_2$ | H | H | 147-148 decomp. | under aromatics | E |
| 55 | $CH_3$ | $CH_3$ | 2-(E—furan-CH:CH) | H | H | oil | 7.63 | E |

TABLE I-continued

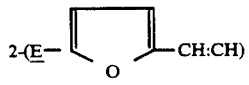

(I)

| Compound No. | R¹ | R² | X | Y | Z | Melting point (°C.) | olefinic* | isomer+ |
|---|---|---|---|---|---|---|---|---|
| 56 | CH₃ | CH₃ | 2-(E—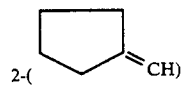—CH:CH) | H | H | 107.5–110 | 6.56 | Z |
| 57 | CH₃ | CH₃ | 3-C₆H₅O | H | H | oil | 7.54 | E |
| 58 | CH₃ | CH₃ | 4-C₆H₅O | H | H | 97–98 | 7.54 | E |
| 59 | CH₃ | CH₃ | 4-C₆H₅O | H | H | oil | 6.64 | Z |
| 60 | CH₃ | CH₃ | ⊕ | ⊕ | H | 124–125 | 7.47 | E |
| 61 | CH₃ | CH₃ | ⊕ | ⊕ | H | 83–84 | 7.63 | E |
| 62 | CH₃ | CH₃ | ⊕ | ⊕ | H | | | E |
| 63 | CH₃ | CH₃ | ⊕ | ⊕ | ⊕ | | | E |
| 64 | CH₃ | CH₃ | ⊕ | ⊕ | H | 122–123 | 7.73 | E |
| 65 | CH₃ | CH₃ | 2-(C₆H₅N(CH₃)) | H | H | oil | under aromatics | |
| 66 | CH₃ | CH₃ | 2-(4-CH₃O—C₆H₄CO) | H | H | oil | 7.32 | E |
| 67 | CH₃ | CH₃ | 2-C₆H₅OCH₂ | H | H | | | E |
| 68 | CH₃ | CH₃ | 2-C₆H₅CH(CH₃)CH₂ | H | H | | | E |
| 69 | CH₃ | CH₃ | 2-C₆H₅C(CH₃)₂CH₂ | H | H | | | E |
| 70 | CH₃ | CH₃ | 2-(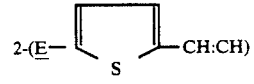CH) | H | H | | | E |
| 71 | CH₃ | CH₃ | 2-(E—4-Cl—C₆H₄CH:CH) | H | H | | | E |
| 72 | CH₃ | CH₂ | 2-(E—4-F—C₆H₄CH:CH) | H | H | | | E |
| 73 | CH₃ | CH₃ | 2-(E—2,6-di-Cl—C₆H₃CH:CH) | H | H | | | E |
| 74 | CH₃ | CH₃ | 2-(E—C₆H₅C(CH₃):C(CH₃)) | H | H | | | E |
| 75 | CH₃ | CH₂ | 2-(E—C₆H₅C(CH₃):CH) | H | H | | | E |
| 76 | CH₃ | CH₃ | 2-(E—C₆H₅CH:C(CH₃)) | H | H | | | E |
| 77 | CH₃ | CH₃ | 2-(E—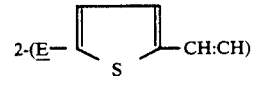—CH:CH) | H | H | | | E |
| 78 | CH₃ | CH₃ | 2-(E—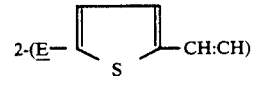—CH:CH) | H | H | | | Z |
| 79 | CH₃ | CH₃ | 2-C₆H₅OCH₂ | H | H | | | Z |
| 80 | CH₃ | CH₃ | 2-C₆H₅OCH(CH₃) | H | H | | | E |
| 81 | CH₃ | CH₃ | 2-C₆H₅OC(CH₃)₂ | H | H | | | E |
| 82 | CH₃ | CH₃ | 2-C₆H₅C(CH₃)₂C(CH₃)₂ | H | H | | | E |
| 83 | CH₃ | CH₃ | 2-(E—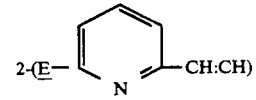—CH:CH) | H | H | | | E |
| 84 | CH₃ | CH₃ | 2-(E—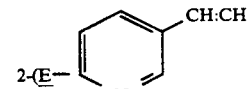—CH:CH) | H | H | | | E |
| 85 | CH₃ | CH₃ | 2-(E—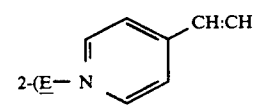—CH:CH) | H | H | | | E |
| 86 | CH₃ | CH₃ | 2(C₆H₅)₂C:CH | H | H | | | E |

TABLE I-continued $$\text{(I)}$$

Structure (I): benzene ring with X, Y, Z substituents and a $C(CO_2R^1)=CH(OR^2)$ group.

| Compound No. | $R^1$ | $R^2$ | X | Y | Z | Melting point (°C.) | olefinic* | isomer+ |
|---|---|---|---|---|---|---|---|---|
| 87 | $CH_3$ | $CH_3$ | 2-(cyclohexylidene-CH) | H | H | | | E |
| 88 | $CH_3$ | $CH_3$ | 2-$C_6H_5CONH$ | H | H | 99–100 | under aromatics | E |
| 89 | $CH_3$ | $CH_3$ | 2-$C_6H_5NHCO$ | H | H | | | E |
| 90 | $CH_3$ | $CH_3$ | 2-(furan-2-CONH) | H | H | | | E |

⊕ Substituents are fused rings.
Thus compound 60 is:

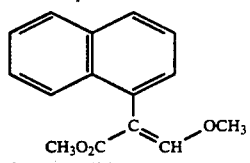

Compound 62 is:

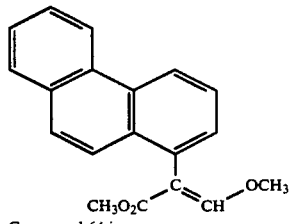

Compound 64 is:

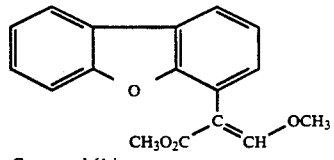

Compound 61 is:

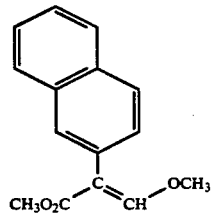

Compound 63:

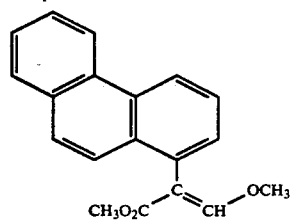

*Chemical shift of singlet from olefinic proton on beta-methoxyacrylate group (ppm from tetramethylsilane). Solvent: $CDCl_3$
+Geometry of the beta-methoxyacrylate group

TABLE II

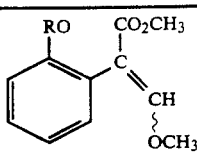

| Compound No. | R | Melting point (°C.) | olefinic* | isomer+ |
|---|---|---|---|---|
| 1 | C$_6$H$_5$ | oil | 7.47 | E |
| 2 | 2-F—C$_6$H$_4$ | | | E |
| 3 | 3-F—C$_6$H$_4$ | | | E |
| 4 | 4-F—C$_6$H$_4$ | 77–78 | 7.50 | E |
| 5 | 2-Cl—C$_6$H$_4$ | oil | 7.46 | E |
| 6 | 3-Cl—C$_6$H$_4$ | oil | 7.45 | E |
| 7 | 4-Cl—C$_6$H$_4$ | oil | 7.48 | E |
| 8 | 2-Br—C$_6$H$_4$ | | | E |
| 9 | 3-Br—C$_6$H$_4$ | | | E |
| 10 | 4-Br—C$_6$H$_4$ | | | E |
| 11 | 2-I—C$_6$H$_4$ | | | E |
| 12 | 3-I—C$_6$H$_4$ | | | E |
| 13 | 4-I—C$_6$H$_4$ | | | E |
| 14 | 2-CH$_3$—C$_6$H$_4$ | | | E |
| 15 | 3-CH$_3$—C$_6$H$_4$ | | | E |
| 16 | 4-CH$_3$—C$_6$H$_4$ | 80–81 | 7.50 | E |
| 17 | 2-CH$_3$CH$_2$—C$_6$H$_4$ | | | E |
| 18 | 3-CH$_3$CH$_2$—C$_6$H$_4$ | | | E |
| 19 | 4-CH$_3$CH$_2$—C$_6$H$_4$ | | | E |
| 20 | 2-(CH$_3$)$_2$CH—C$_6$H$_4$ | | | E |
| 21 | 3-(CH$_3$)$_2$CH—C$_6$H$_4$ | | | E |
| 22 | 4-(CH$_3$)$_2$CH—C$_6$H$_4$ | | | E |
| 23 | 2-(CH$_3$)$_3$C—C$_6$H$_4$ | | | E |
| 24 | 3-(CH$_3$)$_3$C—C$_6$H$_4$ | | | E |
| 25 | 4-(CH$_3$)$_3$C—C$_6$H$_4$ | | | E |
| 26 | 2-CH$_3$O—C$_6$H$_4$ | | | E |
| 27 | 3-CH$_3$O—C$_6$H$_4$ | | | E |
| 28 | 4-CH$_3$O—C$_6$H$_4$ | oil | 7.51 | E |
| 29 | 2-CF$_3$O—C$_6$H$_4$ | | | E |
| 30 | 3-CF$_3$O—C$_6$H$_4$ | | | E |
| 31 | 4-CF$_3$O—C$_6$H$_4$ | | | E |
| 32 | 2-C$_6$H$_5$O—C$_6$H$_4$ | | | E |
| 33 | 3-C$_6$H$_5$O—C$_6$H$_4$ | | | E |
| 34 | 4-C$_6$H$_5$O—C$_6$H$_4$ | | | E |
| 35 | 2-NO$_2$—C$_6$H$_4$ | | | E |
| 36 | 3-NO$_2$—C$_6$H$_4$ | | | E |
| 37 | 4-NO$_2$—C$_6$H$_4$ | | | E |
| 38 | 2-NH$_2$—C$_6$H$_4$ | | | E |
| 39 | 3-NH$_2$—C$_6$H$_4$ | | | E |
| 40 | 4-NH$_2$—C$_6$H$_4$ | | | E |
| 41 | 2-C$_6$H$_5$—C$_6$H$_4$ | | | E |
| 42 | 3-C$_6$H$_5$—C$_6$H$_4$ | | | E |
| 43 | 4-C$_6$H$_5$—C$_6$H$_4$ | | | E |
| 44 | 2-HO$_2$C—C$_6$H$_4$ | | | E |
| 45 | 3-HO$_2$C—C$_6$H$_4$ | | | E |
| 46 | 4-HO$_2$C—C$_6$H$_4$ | | | E |
| 47 | 2-CH$_3$O$_2$C—C$_6$H$_4$ | | | E |
| 48 | 3-CH$_3$O$_2$C—C$_6$H$_4$ | | | E |
| 49 | 4-CH$_3$O$_2$C—C$_6$H$_4$ | | | E |
| 50 | 2-(CN)—C$_6$H$_4$ | | | E |
| 51 | 3-(CN)—C$_6$H$_4$ | | | E |
| 52 | 4-(CN)—C$_6$H$_4$ | | | E |
| 53 | 2-HO—C$_6$H$_4$ | | | E |
| 54 | 3-HO—C$_6$H$_4$ | | | E |
| 55 | 4-HO—C$_6$H$_4$ | | | E |
| 56 | 2-CH$_3$C(O)NH—C$_6$H$_4$ | | | E |
| 57 | 3-CH$_3$C(O)NH—C$_6$H$_4$ | | | E |
| 58 | 4-CH$_3$C(O)NH—C$_6$H$_4$ | | | E |
| 59 | 2,3-di-F—C$_6$H$_3$ | | | E |
| 60 | 2,4-di-F—C$_6$H$_3$ | | | E |
| 61 | 2,5-di-F—C$_6$H$_3$ | | | E |
| 62 | 2,6-di-F—C$_6$H$_3$ | | | E |
| 63 | 3,4-di-F—C$_6$H$_3$ | | | E |
| 64 | 3,5-di-F—C$_6$H$_3$ | | | E |
| 65 | 2,3-di-Cl—C$_6$H$_3$ | | | E |
| 66 | 2,4-di-Cl—C$_6$H$_3$ | oil | 7.48 | E |
| 67 | 2,5-di-Cl—C$_6$H$_3$ | | | E |
| 68 | 2,6-di-Cl—C$_6$H$_3$ | 132–133 | 7.62 | E |
| 69 | 3,4-di-Cl—C$_6$H$_3$ | | | E |
| 70 | 3,5-di-Cl—C$_6$H$_3$ | | | E |
| 71 | 2,3-di-CH$_3$—C$_6$H$_3$ | | | E |
| 72 | 2,4-di-CH$_3$—C$_6$H$_3$ | | | E |
| 73 | 2,5-di-CH$_3$—C$_6$H$_3$ | | | E |

TABLE II-continued

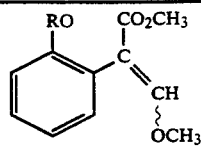

| Compound No. | R | Melting point (°C.) | olefinic* | isomer+ |
|---|---|---|---|---|
| 74 | 2,6-di-$CH_3$—$C_6H_3$ | | | E |
| 75 | 3,4-di-$CH_3$—$C_6H_3$ | | | E |
| 76 | 3,5-di-$CH_3$—$C_6H_3$ | | | E |
| 77 | 2,3-di-$CH_3O$—$C_6H_3$ | | | E |
| 78 | 2,4-di-$CH_3O$—$C_6H_3$ | | | E |
| 79 | 2,5-di-$CH_3O$—$C_6H_3$ | | | E |
| 80 | 2,6-di-$CH_3O$—$C_6H_3$ | | | E |
| 81 | 3,4-di-$CH_3O$—$C_6H_3$ | | | E |
| 82 | 3,5-di-$CH_3O$—$C_6H_3$ | | | E |
| 83 | 2-F,3-Cl—$C_6H_3$ | | | E |
| 84 | 2-F,4-Cl—$C_6H_3$ | | | E |
| 85 | 2-F,5-Cl—$C_6H_3$ | | | E |
| 86 | 2-F,6-Cl—$C_6H_3$ | | | E |
| 87 | 3-F,4-Cl—$C_6H_3$ | | | E |
| 88 | 3-F,5-Cl—$C_6H_3$ | | | E |
| 89 | 2-Cl-3-F—$C_6H_3$ | | | E |
| 90 | 2-Cl,4-F—$C_6H_3$ | | | E |
| 91 | 2-Cl,5-F—$C_6H_3$ | | | E |
| 92 | 3-Cl,4-F—$C_6H_3$ | | | E |
| 93 | 2-F,3-$CH_3$—$C_6H_3$ | | | E |
| 94 | 2-F,4-$CH_3$—$C_6H_3$ | | | E |
| 95 | 2-F,5-$CH_3$—$C_6H_3$ | | | E |
| 96 | 2-F,6-$CH_3$—$C_6H_3$ | | | E |
| 97 | 3-F,4-$CH_3$—$C_6H_3$ | | | E |
| 98 | 3-F,5-$CH_3$—$C_6H_3$ | | | E |
| 99 | 2-$CH_3$,3-F—$C_6H_3$ | | | E |
| 100 | 2-$CH_3$,4-F—$C_6H_3$ | | | E |
| 101 | 2-$CH_3$,5-F—$C_6H_3$ | | | E |
| 102 | 3-$CH_3$,4-F—$C_6H_3$ | | | E |
| 103 | 2-F,3-$CH_3O$—$C_6H_3$ | | | E |
| 104 | 2-F,4-$CH_3O$—$C_6H_3$ | | | E |
| 105 | 2-F,5-$CH_3O$—$C_6H_3$ | | | E |
| 106 | 2-F,6-$CH_3O$—$C_6H_3$ | | | E |
| 107 | 3-F,4-$CH_3O$—$C_6H_3$ | | | E |
| 108 | 3-F,5-$CH_3O$—$C_6H_3$ | | | E |
| 109 | 2-$CH_3O$,3-F—$C_6H_3$ | | | E |
| 110 | 2-$CH_3O$,4-F—$C_6H_3$ | | | E |
| 111 | 2-$CH_3O$,5-F—$C_6H_3$ | | | E |
| 112 | 3-$CH_3O$,4-F—$C_6H_3$ | | | E |
| 113 | 2-Cl,3-$CH_3$—$C_6H_3$ | | | E |
| 114 | 2-Cl,4-$CH_3$—$C_6H_3$ | | | E |
| 115 | 2-Cl,5-$CH_3$—$C_6H_3$ | | | E |
| 116 | 2-Cl,6-$CH_3$—$C_6H_3$ | | | E |
| 117 | 3-Cl,4-$CH_3$—$C_6H_3$ | | | E |
| 118 | 3-Cl,5-$CH_3$—$C_6H_3$ | | | E |
| 119 | 2-$CH_3$,3-Cl—$C_6H_3$ | | | E |
| 120 | 2-$CH_3$,4-Cl—$C_6H_3$ | | | E |
| 121 | 2-$CH_3$,5-Cl—$C_6H_3$ | | | E |
| 122 | 3-$CH_3$,4-Cl—$C_6H_3$ | | | E |
| 123 | 2-Cl,3-$CH_3O$—$C_6H_3$ | | | E |
| 124 | 2-Cl,4-$CH_3O$—$C_6H_3$ | | | E |
| 125 | 2-Cl,5-$CH_3O$—$C_6H_3$ | | | E |
| 126 | 2-Cl,6-$CH_3O$—$C_6H_3$ | | | E |
| 127 | 3-Cl,4-$CH_3O$—$C_6H_3$ | | | E |
| 128 | 3-Cl,5-$CH_3O$—$C_6H_3$ | | | E |
| 129 | 2-$CH_3O$,3-Cl—$C_6H_3$ | | | E |
| 130 | 2-$CH_3O$,4-Cl—$C_6H_3$ | | | E |
| 131 | 2-$CH_3O$,5-Cl—$C_6H_3$ | | | E |
| 132 | 3-$CH_3O$,4-Cl—$C_6H_3$ | | | E |
| 133 | 2-$CH_3$,3-$CH_3O$—$C_6H_3$ | | | E |
| 134 | 2-$CH_3$,4-$CH_3O$—$C_6H_3$ | | | E |
| 135 | 2-$CH_3$,5-$CH_3O$—$C_6H_3$ | | | E |
| 136 | 2-$CH_3$,6-$CH_3O$—$C_6H_3$ | | | E |
| 137 | 3-$CH_3$,4-$CH_3O$—$C_6H_3$ | | | E |
| 138 | 3-$CH_3$,5-$CH_3O$—$C_6H_3$ | | | E |
| 139 | 2-$CH_3O$,3-$CH_3$—$C_6H_3$ | | | E |
| 140 | 2-$CH_3O$,4-$CH_3$—$C_6H_3$ | | | E |
| 141 | 2-$CH_3O$,5-$CH_3$—$C_6H_3$ | | | E |
| 142 | 3-$CH_3O$,4-$CH_3$—$C_6H_3$ | | | E |
| 143 | 2,4,6-tri-F—$C_6H_2$ | | | E |
| 144 | 2,4,6-tri-Cl—$C_6H_2$ | | | E |
| 145 | 2,4,6-tri-$CH_3$—$C_6H_2$ | | | E |
| 146 | 2,6-di-F,4-Cl—$C_6H_2$ | | | E |

TABLE II-continued

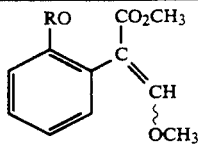

| Compound No. | R | Melting point (°C.) | olefinic* | isomer+ |
|---|---|---|---|---|
| 147 | 2,6-di-Me,4-F—$C_6H_2$ | | | E |
| 148 | 2,6-di-Cl,4-F—$C_6H_2$ | | | E |
| 149 | 2,3,5,6-tetra-Cl—$C_6H$ | | | E |
| 150 | Pentafluorophenyl | | | E |
| 151 | Pentachlorophenyl | | | E |
| 152 | H | | | E |
| 153 | $CH_3$ | oil | 7.52 | E |
| 154 | $CH_3CH_2$ | | | E |
| 155 | $CH_3CH_2CH_2$ | | | E |
| 156 | $(CH_3)_2CH$ | | | E |
| 157 | $CH_3CH_2CH_2CH_2$ | | | E |
| 158 | $(CH_3)_3C$ | | | E |
| 159 | Cyclohexyl | oil | 7.38 | E |
| 160 | $CH_2$:$CHCH_2$ | oil | 7.46 | E |
| 161 | E—$C_6H_5CH$:$CHCH_2$ | oil | 7.46 | E |
| 162 | $CH_2$:$C(CH_3)CH_2$ | | | E |
| 163 | E—$CH_3CH$:$CHCH_2$ | | | E |
| 164 | 2-tetrahydropyranyl | | | E |
| 165 | 2-pyridyl | oil | 7.43 | E |
| 166 | 3-pyridyl | | | E |
| 167 | 4-pyridyl | | | E |
| 168 | 2-(5'-$CF_3$-pyridyl) | | | E |
| 169 | 2-pyrimidyl | | | E |
| 170 | 4-pyrimidyl | | | E |
| 171 | 5-pyrimidyl | | | E |
| 172 | 3,4-methylenedioxyphenyl | | | E |
| 173 | 1-naphthyl | | | E |
| 174 | 2-naphthyl | | | E |
| 175 | $CH_3SCH_2$ | | | E |
| 176 | $C_6H_5SCH_2$ | | | E |
| 177 | $C_6H_5CH_2$ | 76-77 | 7.49 | E |
| 178 | $C_6H_5C(CH_3)_2$ | | | E |
| 179 | 4-Cl—$C_6H_4C(CH_3)_2$ | | | E |
| 180 | $CH_3$ | 74-75 | 6.55 | Z |
| 181 | $C_6H_5$ | oil | 6.60 | Z |

*Chemical shift of singlet from olefinic proton on beta-methoxyacrylate group (ppm from tetramethylsilane). Solvent: $CDCl_3$
+Geometry of beta-methoxyacrylate group Table III below embraces compounds of the general formula:

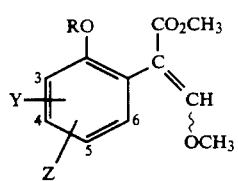

wherein the group R includes all the groups R listed in Table II for each of the following substitution patterns on the phenyl ring shown above. The acrylate group may have either the E- or the Z-geometry in each case.

TABLE III

| Y | Z |
|---|---|
| 3-F | H |
| 4-F | H |
| 5-F | H |
| 6-F | H |
| 3-Cl | H |
| 4-Cl | H |
| 5-Cl | H |
| 6-Cl | H |
| 3-$CH_3$ | H |
| 4-$CH_3$ | H |
| 5-$CH_3$ | H |
| 6-$CH_3$ | H |
| 3-$NO_2$ | H |
| 4-$NO_2$ | H |
| 5-$NO_2$ | H |
| 6-$NO_2$ | H |
| 5-$CF_3$ | H |
| 3-$NO_2$ | 5-Cl |
| 3-$NO_2$ | 5-$NO_2$ |
| 5-$SCH_3$ | H |
| 4-$CH_3O$ | 5-$CH_3O$ |
| 4-$(CH_3)_2N$ | H |
| 4,5-methylenedioxy | |

Specific examples of compounds of the type shown in Table III are as follows:

| Compound No. | R | Y | Z | Melting Point (°C) | Olefinic* | Isomer+ |
|---|---|---|---|---|---|---|
| 1 | $C_6H_5$ | 3-Cl | H | | | E |
| 2 | $C_6H_5$ | 4-$NO_2$ | H | | | E |
| 3 | $C_6H_5$ | 5-Cl | H | oil | 7.47 | E |
| 4 | $C_6H_5$ | 6-$NO_2$ | H | | | E |

-continued

| Compound No. | R | Y | Z | Melting Point (°C) | Olefinic* | Isomer+ |
|---|---|---|---|---|---|---|
| 5 | C₆H₅ | 5-NO₂ | H | oil | 7.60 | E |

*Chemical shift of singlet from olefinic proton on beta-methoxyacrylate group (ppm from tetramethylsilane). Solvent CDCl₃
+Geometry of beta-methoxyacrylate group.

TABLE IV

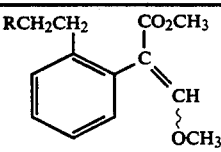

| Compound No. | R | Melting point (°C) | olefinic* | isomer+ |
|---|---|---|---|---|
| 1 | C₆H₅ | oil | 7.59 | E |
| 2 | 2-F-C₆H₄ | | | E |
| 3 | 3-F-C₆H₄ | | | E |
| 4 | 4-F-C₆H₄ | | | E |
| 5 | 2-Cl-C₆H₄ | | | E |
| 6 | 3-Cl-C₆H₄ | | | E |
| 7 | 4-Cl-C₆H₄ | | | E |
| 8 | 2-Br-C₆H₄ | | | E |
| 9 | 3-Br-C₆H₄ | | | E |
| 10 | 4-Br-C₆H₄ | | | E |
| 11 | 2-I-C₆H₄ | | | E |
| 12 | 3-I-C₆H₄ | | | E |
| 13 | 4-I-C₆H₄ | | | E |
| 14 | 2-CH₃—C₆H₄ | | | E |
| 15 | 3-CH₃—C₆H₄ | | | E |
| 16 | 4-CH₃—C₆H₄ | | | E |
| 17 | 2-CH₃CH₂—C₆H₄ | | | E |
| 18 | 3-CH₃CH₂—C₆H₄ | | | E |
| 19 | 4-CH₃CH₂—C₆H₄ | | | E |
| 20 | 2-(CH₃)₂CH—C₆H₄ | | | E |
| 21 | 3-(CH₃)₂CH—C₆H₄ | | | E |
| 22 | 4-(CH₃)₂CH—C₆H₄ | | | E |
| 23 | 2-(CH₃)₃C—C₆H₄ | | | E |
| 24 | 3-(CH₃)₃C—C₆H₄ | | | E |
| 25 | 4-(CH₃)₃C—C₆H₄ | | | E |
| 26 | 2-CH₃O—C₆H₄ | | | E |
| 27 | 3-CH₃O—C₆H₄ | | | E |
| 28 | 4-CH₃O—C₆H₄ | | | E |
| 29 | 2-CF₃O—C₆H₄ | | | E |
| 30 | 3-CF₃O—C₆H₄ | | | E |
| 31 | 4-CF₃O—C₆H₄ | | | E |
| 32 | 2-C₆H₅O—C₆H₄ | | | E |
| 33 | 3-C₆H₅O—C₆H₄ | | | E |
| 34 | 4-C₆H₅O—C₆H₄ | | | E |
| 35 | 2-NO₂—C₆H₄ | | | E |
| 36 | 3-NO₂—C₆H₄ | | | E |
| 37 | 4-NO₂—C₆H₄ | | | E |
| 38 | 2-NH₂—C₆H₄ | | | E |
| 39 | 3-NH₂—C₆H₄ | | | E |
| 40 | 4-NH₂—C₆H₄ | | | E |
| 41 | 2-C₆H₅—C₆H₄ | | | E |
| 42 | 3-C₆H₅—C₆H₄ | | | E |
| 43 | 4-C₆H₅—C₆H₄ | | | E |
| 44 | 2-HO₂C—C₆H₄ | | | E |
| 45 | 3-HO₂C—C₆H₄ | | | E |
| 46 | 4-HO₂C—C₆H₄ | | | E |
| 47 | 2-CH₃O₂C—C₆H₄ | | | E |
| 48 | 3-CH₃O₂C—C₆H₄ | | | E |
| 49 | 4-CH₃O₂C—C₆H₄ | | | E |
| 50 | 2-(CN)—C₆H₄ | | | E |
| 51 | 3-(CN)—C₆H₄ | | | E |
| 52 | 4-(CN)—C₆H₄ | | | E |
| 53 | 2-HO—C₆H₄ | | | E |
| 54 | 3-HO—C₆H₄ | | | E |
| 55 | 4-HO—C₆H₄ | | | E |
| 56 | 2-CH₃C(O)NH—C₆H₄ | | | E |
| 57 | 3-CH₃C(O)NH—C₆H₄ | | | E |
| 58 | 4-CH₃C(O)NH—C₆H₄ | | | E |
| 59 | 2,3-di-F—C₆H₃ | | | E |
| 60 | 2,4-di-F—C₆H₃ | | | E |

TABLE IV-continued

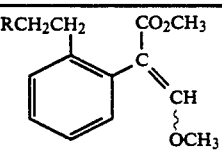

| Compound No. | R | Melting point (°C.) | olefinic* | isomer+ |
|---|---|---|---|---|
| 61 | 2,5-di-F—C₆H₃ | | | E |
| 62 | 2,6-di-F—C₆H₃ | | | E |
| 63 | 3,4-di-F—C₆H₃ | | | E |
| 64 | 3,5-di-F—C₆H₃ | | | E |
| 65 | 2,3-di-Cl—C₆H₃ | | | E |
| 66 | 2,4-di-Cl—C₆H₃ | | | E |
| 67 | 2,5-di-Cl—C₆H₃ | | | E |
| 68 | 2,6-di-Cl—C₆H₃ | | | E |
| 69 | 3,4-di-Cl—C₆H₃ | | | E |
| 70 | 3,5-di-Cl—C₆H₃ | | | E |
| 71 | 2,3-di-CH₃—C₆H₃ | | | E |
| 72 | 2,4-di-CH₃—C₆H₃ | | | E |
| 73 | 2,5-di-CH₃—C₆H₃ | | | E |
| 74 | 2,6-di-CH₃—C₆H₃ | | | E |
| 75 | 3,4-di-CH₃—C₆H₃ | | | E |
| 76 | 3,5-di-CH₃—C₆H₃ | | | E |
| 77 | 2,3-di-CH₃O—C₆H₃ | | | E |
| 78 | 2,4-di-CH₃O—C₆H₃ | | | E |
| 79 | 2,5-di-CH₃O—C₆H₃ | | | E |
| 80 | 2,6-di-CH₃O—C₆H₃ | | | E |
| 81 | 3,4-di-CH₃O—C₆H₃ | | | E |
| 82 | 3,5-di-CH₃O—C₆H₃ | | | E |
| 83 | 2-F,3-Cl—C₆H₃ | | | E |
| 84 | 2-F,4-Cl—C₆H₃ | | | E |
| 85 | 2-F,5-Cl—C₆H₃ | | | E |
| 86 | 2-F,6-Cl—C₆H₃ | | | E |
| 87 | 3-F,4-Cl—C₆H₃ | | | E |
| 88 | 3-F,5-Cl—C₆H₃ | | | E |
| 89 | 2-Cl-3-F—C₆H₃ | | | E |
| 90 | 2-Cl,4-F—C₆H₃ | | | E |
| 91 | 2-Cl,5-F—C₆H₃ | | | E |
| 92 | 3-Cl,4-F—C₆H₃ | | | E |
| 93 | 2-F,3-CH₃—C₆H₃ | | | E |
| 94 | 2-F,4-CH₃—C₆H₃ | | | E |
| 95 | 2-F,5-CH₃—C₆H₃ | | | E |
| 96 | 2-F,6-CH₃—C₆H₃ | | | E |
| 97 | 3-F,4-CH₃—C₆H₃ | | | E |
| 98 | 3-F,5-CH₃—C₆H₃ | | | E |
| 99 | 2-CH₃,3-F—C₆H₃ | | | E |
| 100 | 2-CH₃,4-F—C₆H₃ | | | E |
| 101 | 2-CH₃,5-F—C₆H₃ | | | E |
| 102 | 3-CH₃,4-F—C₆H₃ | | | E |
| 103 | 2-F,3-CH₃O—C₆H₃ | | | E |
| 104 | 2-F,4-CH₃O—C₆H₃ | | | E |
| 105 | 2-F,5-CH₃O—C₆H₃ | | | E |
| 106 | 2-F,6-CH₃O—C₆H₃ | | | E |
| 107 | 3-F,4-CH₃O—C₆H₃ | | | E |
| 108 | 3-F,5-CH₃O—C₆H₃ | | | E |
| 109 | 2-CH₃O,3-F—C₆H₃ | | | E |
| 110 | 2-CH₃O,4-F—C₆H₃ | | | E |
| 111 | 2-CH₃O,5-F—C₆H₃ | | | E |
| 112 | 3-CH₃O,4-F—C₆H₃ | | | E |
| 113 | 2-Cl,3-CH₃—C₆H₃ | | | E |
| 114 | 2-Cl,4-CH₃—C₆H₃ | | | E |
| 115 | 2-Cl,5-CH₃—C₆H₃ | | | E |
| 116 | 2-Cl,6-CH₃—C₆H₃ | | | E |
| 117 | 3-Cl,4-CH₃—C₆H₃ | | | E |
| 118 | 3-Cl,5-CH₃—C₆H₃ | | | E |
| 119 | 2-CH₃,3-Cl—C₆H₃ | | | E |
| 120 | 2-CH₃,4-Cl—C₆H₃ | | | E |
| 121 | 2-CH₃,5-Cl—C₆H₃ | | | E |
| 122 | 3-CH₃,4-Cl—C₆H₃ | | | E |
| 123 | 2-Cl,3-CH₃O—C₆H₃ | | | E |
| 124 | 2-Cl,4-CH₃O—C₆H₃ | | | E |
| 125 | 2-Cl,5-CH₃O—C₆H₃ | | | E |
| 126 | 2-Cl,6-CH₃O—C₆H₃ | | | E |
| 127 | 3-Cl,4-CH₃O—C₆H₃ | | | E |
| 128 | 3-Cl,5-CH₃O—C₆H₃ | | | E |
| 129 | 2-CH₃O,3-Cl—C₆H₃ | | | E |
| 130 | 2-CH₃O,4-Cl—C₆H₃ | | | E |
| 131 | 2-CH₃O,5-Cl—C₆H₃ | | | E |

TABLE IV-continued

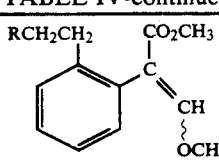

| Compound No. | R | Melting point (°C.) | olefinic* | isomer+ |
|---|---|---|---|---|
| 132 | 3-CH₃O,4-Cl—C₆H₃ | | | E |
| 133 | 2-CH₃,3-CH₃O—C₆H₃ | | | E |
| 134 | 2-CH₃,4-CH₃O—C₆H₃ | | | E |
| 135 | 2-CH₃,5-CH₃O—C₆H₃ | | | E |
| 136 | 2-CH₃,6-CH₃O—C₆H₃ | | | E |
| 137 | 3-CH₃,4-CH₃O—C₆H₃ | | | E |
| 138 | 3-CH₃,5-CH₃O—C₆H₃ | | | E |
| 139 | 2-CH₃O,3-CH₃—C₆H₃ | | | E |
| 140 | 2-CH₃O,4-CH₃—C₆H₃ | | | E |
| 141 | 2-CH₃O,5-CH₃—C₆H₃ | | | E |
| 142 | 3-CH₃O,4-CH₃—C₆H₃ | | | E |
| 143 | 2,4,6-tri-F—C₆H₂ | | | E |
| 144 | 2,4,6-tri-Cl—C₆H₂ | | | E |
| 145 | 2,4,6-tri-CH₃—C₆H₂ | | | E |
| 146 | 2,6-di-F,4-Cl—C₆H₂ | | | E |
| 147 | 2,6-di-Me,4-F—C₆H₂ | | | E |
| 148 | 2,6-di-Cl,4-F—C₆H₂ | | | E |
| 149 | 2,3,5,6-tetra-Cl—C₆H | | | E |
| 150 | Pentafluorophenyl | | | E |
| 151 | Pentachlorophenyl | | | E |
| 152 | H | | | E |
| 153 | CH₃ | | | E |
| 154 | CH₃CH₂ | | | E |
| 155 | CH₃CH₂CH₂ | | | E |
| 156 | (CH₃)₂CH | | | E |
| 157 | CH₃CH₂CH₂CH₂ | | | E |
| 158 | (CH₃)₃C | | | E |
| 159 | Cyclohexyl | | | E |
| 160 | CH₂:CHCH₂ | | | E |
| 161 | E—C₆H₅CH:CHCH₂ | | | E |
| 162 | CH₂:C(CH₃)CH₂ | | | E |
| 163 | E—CH₃CH:CHCH₂ | | | E |
| 164 | 2-tetrahydropyranyl | | | E |
| 165 | 2-pyridyl | | | E |
| 166 | 3-pyridyl | | | E |
| 167 | 4-pyridyl | | | E |
| 168 | 2-(5'-CF₃-pyridyl) | | | E |
| 169 | 2-pyrimidyl | | | E |
| 170 | 4-pyrimidyl | | | E |
| 171 | 5-pyrimidyl | | | E |
| 172 | 3,4-methylenedioxyphenyl | | | E |
| 173 | 1-naphthyl | | | E |
| 174 | 2-naphthyl | | | E |
| 175 | CH₃SCH₂ | | | E |
| 176 | C₆H₅SCH₂ | | | E |
| 177 | C₆H₅ | oil | 6.24 | Z |
| 178 | 2-furyl | | | E |
| 179 | 3-furyl | | | E |
| 180 | 2-thiophenyl | | | E |
| 181 | 3-thiophenyl | | | E |
| 182 | 2-pyrrolyl | | | E |
| 183 | 3-pyrrolyl | | | E |
| 184 | C₆H₅CH₂ | | | E |
| 185 | C₆H₅CH(CH₃) | | | E |
| 186 | C₆H₅C(CH₃)₂ | | | E |

*Chemical shift of singlet from olefinic proton on beta-methoxyacrylate group (ppm from tetramethylsilane). Solvent: CDCl₃
+Geometry of beta-methoxyacrylate group

TABLE V

Table V embraces compounds of the general formula:

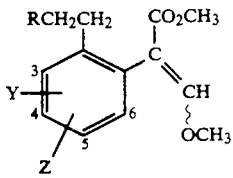

wherein the group R includes all the group R listed in Table IV for each of the following substitution patterns on the phenyl rings shown above. The acrylate group may have either the E- or the Z-geometry in each case.

| Y | Z |
|---|---|
| 3-F | H |
| 4-F | H |
| 5-F | H |
| 6-F | H |
| 3-Cl | H |
| 4-Cl | H |
| 5-Cl | H |
| 6-Cl | H |
| 3-CH₃ | H |
| 4-CH₃ | H |
| 5-CH₃ | H |
| 6-CH₃ | H |
| 3-NO₂ | H |
| 4-NO₂ | H |
| 5-NO₂ | H |
| 6-NO₂ | H |
| 5-CF₃ | H |
| 3-NO₂ | 5-Cl |
| 3-NO₂ | 5-NO₂ |
| 5-SCH₃ | H |
| 4-CH₃O | 5-CH₃O |
| 4-(CH₃)₂N | H |
| 4,5-methylenedioxy | |

TABLE VI: SELECTED PROTON NMR DATA

Table VI shows selected proton nmr data for certain compounds described in Tables I to V and characterised therein as oils. Chemical shifts are measured in ppm from tetramethylsilane, and deuterochloroform was used as solvent throughout. The following abbreviations are used:

| | |
|---|---|
| br = broad | t = triplet |
| s = singlet | q = quartet |
| d = doublet | m = multiplet |

| Compound No. | Table No. | |
|---|---|---|
| 3 | I | 1.27(3H, t J7Hz), 3.83(3H, s), 4.21 (2H, q J7Hz), 7.32(5H, br s), 7.53 (1H, s) |
| 4 | I | 1.30(3H, t J7Hz), 3.72(3H, s), 4.06 (2H, q J 7Hz), 7.31(5H, br s), 7.62 (1H, s). |
| 5 | I | 1.27 and 1.31(2 triplets J 7Hz, each 3H), 4.08 and 4.22(2 quartets J 7Hz, each 2H), 7.33(5H, br s), 7.62(1H, s). |
| 6 | I | 3.81(3H, s), 5.21(2H, s), 7.34 (10H, br s), 7.56(1H, s). |
| 8 | I | 1.49(9H, s), 3.82(3H, s), 7.31 (5H, br s), 7.44(1H, s). |
| 15 | I | 1.42(9H, s), 3.70(3H, s), 6.50 (2H, s), 7.37(1H, s). |

-continued

| Compound No. | Table No. | |
|---|---|---|
| 16 | I | 1.28(9H, s), 3.83(3H, s), 6.46 (2H, s), 7.87(1H, s). |
| 20 | I | 3.67(3H, s), 3.79(3H, s), 5.18 (1H, dd J11 and 1Hz), 5.65(1H, dd J 18 and 1Hz), 6.68(1H, dd J 18 and 11Hz), 7.57(1H, s). |
| 26 | I | 3.78(3H, s), 3.95(3H, s), 6.70 (1H, s). |
| 28 | I | 2.18(3H, s), 3.68(3H, s), 3.82 (3H, s), 7.55(1H, s). |
| 30 | I | 3.68(3H, s), 3.83(6H, s), 7.25–7.6 (3H, m), 7.52(1H, s), 7.9–8.1 (1H, m). |
| 40 | I | 3.60(3H, s), 3.66(3H, s), 3.87 (2H, s), 7.48(1H, s). |
| 42 | I | 3.60(3H, s), 3.70(3H, s), 3.75 (3H, s), 3.80(2H, s), 7.50(1H, s). |
| 45 | I | 3.6(3H, s), 3.75(3H, s), 7.0–8.15 (5H, m), |
| 52 | I | 3.66(3H, s), 3.76(3H, s), 7.51 (1H, s). |
| 53 | I | 3.56(3H, s), 3.73(3H, s), 7.1–7.7 (9H, m), 7.9–8.1(1H, m). |
| 57 | I | 3.73(3H, s), 3.85(3H, s), 7.54 (1H, s). |
| 59 | I | 3.77(3H, s), 3.91(3H, s), 6.64 (1H, s). |
| 65 | I | 3.05(3H, s), 3.43(3H, s), 3.61 (3H, s). |
| 66 | I | 3.53(3H, s), 3.67(3H, s), 3.85 (3H, s), 7.32(1H, s). |
| 5 | II | 3.63(3H, s), 3.78(3H, s), 6.80–7.40 (8H, m), 7.46(1H, s). |
| 6 | II | 3.60(3H, s), 3.76(3H, s), 6.8–7.0 (4H, m), 7.14–7.32(4H, m), 7.45(1H, s). |
| 7 | II | 3.62(3H, s), 3.77(3H, s), 7.48 (1H, s). |
| 28 | II | 3.66(3H, s), 3.80(3H, s), 3.82(3H, s), 6.8–7.3(8H, m), 7.51(1H, s). |
| 66 | II | 3.65(3H, s), 3.79(3H, s), 7.48 (1H, s). |
| 153 | II | 3.70(3H, s), 3.79(3H, s), 3.82 (3H, s), 7.53(1H, s). |
| 159 | II | 1.1–2.1(10H, m), 3.65(3H, s), 3.76 (3H, s), 4.20(1H, br s), 7.38 (1H, s). |
| 160 | II | 3.63(3H, s), 3.80(3H, s), 4.51 (2H, d), 5.05–6.39(3H, m), 6.70–7.35 (4H, m), 7.46(1H, s). |
| 161 | II | 3.60(3H, s), 3.74(3H, s), 4.66 (2H, d), 6.00–7.40(11H, m), 7.46 (1H, s). |
| 181 | II | 3.54(3H, s), 3.88(3H, s), 6.60 (1H, s). |
| 165 | II | 3.55(3H, s), 3.74(3H, s), 6.80 (1H, d), 6.95(1H, m), 7.15–7.40 (4H, m), 7.43(1H, s), 7.65(1H, m), 8.19(1H, m). |
| 3 | III | 3.61(3H, s), 3.78(3H, s), 6.8–7.3 (8H, m), 7.47(1H, s). |
| 5 | III | 3.69(3H, s), 3.88(3H, s), 6.84 (1H, d), 7.60(1H, s), 8.10(1H, dd), 8.20(1H, d). |

The compounds of the invention having the general formula (I) can be prepared from substituted benzenes of general formula (IV) by the steps shown in Scheme I. Throughout Scheme I the terms $R^1$, $R^2$, X, Y and Z are as defined above, L is a halogen (iodine, bromine or chlorine) atom or a hydrogen atom, and M is a metal atom (such as a lithium atom) or a metal atom plus as associated halogen atom (such as MgI, MgBr or MgCl).

Thus compounds of general formula (I) in which $R^1$ and $R^2$ are not hydrogen atoms can be prepared by treatment of ketoesters of general formula (II : $R^1$ is not a hydrogen atom) with phosphoranes of general formula (V : $R^2$ is not a hydrogen atom) in a convenient solvent such as diethyl ether (see, for example, W Steglich, G Schramm, T Anke and F Oberwinkler, EP 0044448, 4.7.80).

Ketoesters of general formula (II : $R^1$ is not a hydrogen atom) can be prepared by treatment of metallated species (III) with an oxalate (VI, $R^1$ is not a hydrogen atom) in a suitable solvent such as diethyl ether or tetrahydrofuran. The preferred method often involves slow addition of a solution of the metallated species (III) to a stirred solution of an excess of the oxalate (VI) (See, for example, L M Weinstock, R B Currie and A V Lovell, *Synthetic Communications*, 1981, 11, 943, and references therein).

The metallated species (III) in which M=MgI, MgBr or MgCl (Grignard reagents) can be prepared by standard methods from the corresponding aromatic halides (IV) in which L=I, Br or Cl respectively. With certain substituents X, Y and Z, the metallated species (III) in which M=Li can be prepared by direct lithiation of compounds (IV) in which L=H using a strong lithium base such as n-butyl-lithium or lithium di-isopropylamide (see, for example, H W Gschwend and H R Rodriquez, *Organic Reactions*, 1979, 26, 1).

Compounds of general formula (IV) can be prepared by standard methods described in the chemical literature.

Scheme I

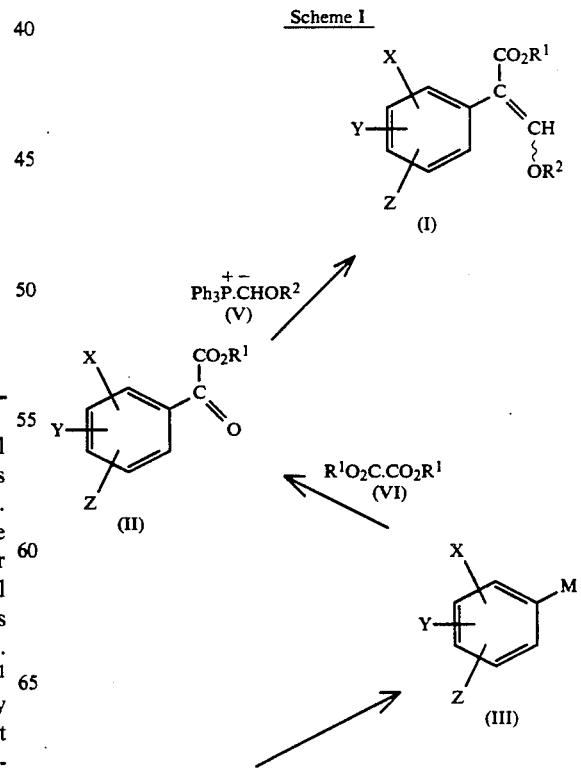

-continued
Scheme I

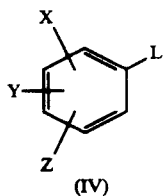
(IV)

Alternative methods for the preparation of ketoesters of general formula (II : $R^1$ is not a hydrogen atom) are described in the chemical literature (see, for example, D C Atkinson, K E Godfrey, B Meek, J F Saville and M R Stillings, *J. Med. Chem.*, 1983, 26, 1353; D Horne, J Gaudino and W J Thompson, *Tetrahedron Lett.*, 1984, 25, 3529; and G P Axiotis, *Tetrahedron Lett.*, 1981, 22, 1509).

Alternative approaches to the compounds of the invention of general formula (I) are outlined in Scheme II. Throughout Scheme II the terms $R^1$, $R^2$, X, Y and Z are as defined above.

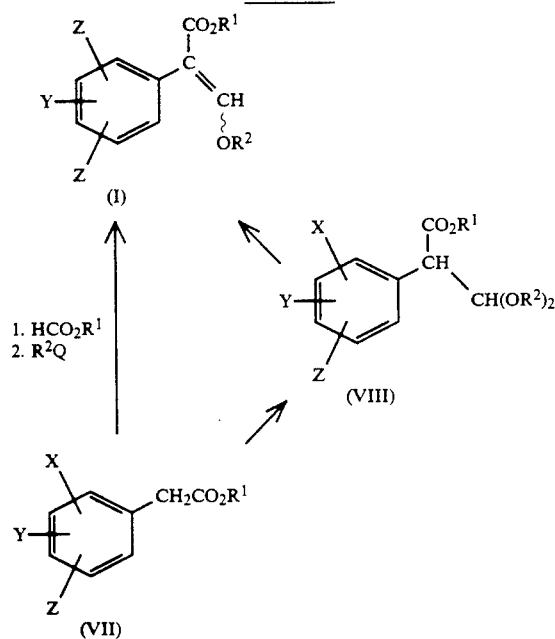

Compounds of general formula (I) in which $R^1$ is not a hydrogen atom can be prepared by treatment of phenylacetates of general formula (VII : $R^1$ is not a hydrogen atom) with a base and a formic ester such as methyl formate or $HCO_2R^1$ wherein $R^1$ is as defined above but is not a hydrogen atom, in a suitable solvent. If the reaction is quenched with a species of general formula $R^2Q$, wherein $R^2$ is as defined above but it is not a hydrogen atom and Q is a leaving group such as a halogen atom, compounds of general formula (I) in which $R^2$ is not a hydrogen atom may be obtained. If, on the other hand, the reaction is quenched with water, compounds of general formula (I) in which $R^2$=H are obtained.

Compounds of general formula (I) in which $R^2$=H can be converted into compounds (I) in which $R^2$ is not a hydrogen atom by successive treatment with a base (such as potassium carbonate or sodium hydride) and a species of general formula $R^2Q$, wherein $R^2$ and Q are as defined above, in a suitable solvent.

Furthermore, compounds of general formula (I) in which neither $R^1$ nor $R^2$ are hydrogen atoms can be made from acetals of general formula (VIII) in which neither $R^1$ nor $R^2$ are hydrogen atoms under either basic or acidic conditions, in suitable solvents and at suitable temperatures. An example of a suitable base is lithium di-isopropylamide, and potassium hydrogen sulphate is an example of a suitable acidic reagent (see T Yamada, H Hagiwara and H Uda, *Journal of the Chem. Soc., Chem. Commun.*, 1980, 838, and references therein).

Acetals of general formula (VIII) in which neither $R^1$ nor $R^2$ are hydrogen atoms may be prepared from phenylacetic esters of general formula (VII : $R^1$ is not a hydrogen atom) by treatment of alkyl silyl ketone acetal derivatives of the species (VII) with trialkylorthoformates in the presence of a Lewis acid in a suitable solvent and at a suitable temperature (see, for example, K Saigo, M Osaki and T Mukaiyama, *Chem. Letts.*, 1976, 769).

Alternative approaches to the compounds of the invention of general formula (I) are outlined in Scheme III. Throughout Scheme III the terms $R^1$, $R^2$, X, Y and Z are as defined above.

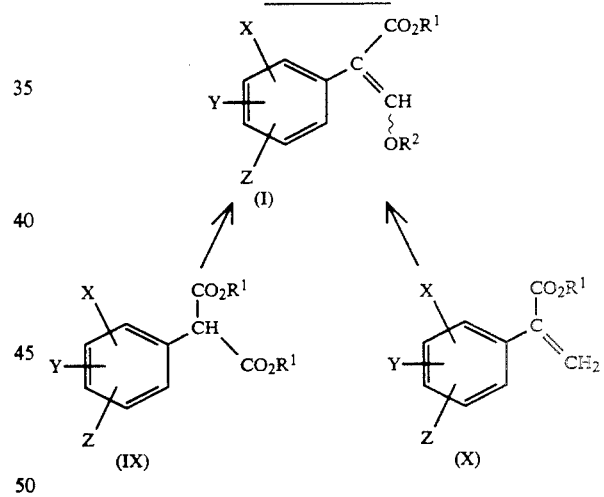

Thus, compounds of general formula (I) in which $R^1$ is not a hydrogen atom and $R^2$=H can be made by partial reduction of malonate derivative (IX : $R^1$ is not a hydrogen atom) using a reducing agent such as lithium aluminum hydride in a suitable solvent such as diethyl ether (see, for example, M Barczai-Beke, G Dornyei, G Toth, J Tamas and Cs Szantay, *Tetrahedron*, 1976, 32, 1153, and references therein).

In addition, compounds of general formula (I) can be made from acrylic acid derivatives of general formula (X) by successive treatment with bromine, a reagent of general formula $R^2OM$, wherein $R^2$ and M are as defined above, and sodium hydrogen sulphate or a related chemical (see, for example G Shaw and R N Warrener, *Journal of the Chemical Society*, 1958, 153, and references therein).

Compounds of general formulae (VII), (IX) and (X) can be prepared by standard methods described in the chemical literature.

All the foregoing processes, either in full, or in any part (step) or parts (steps) thereof, in any combination thereof, are deemed to constitute processes according to the invention.

The compounds and metal complexes of the invention are active fungicides, particularly against the diseases:

*Pyricularia oryzae* on rice.

*Puccinia recondita, Puccinia striiformis* and other rusts on wheat, *Puccinia hordei, Puccinia striiformis* and other rusts on barley, and rusts on other hosts e.g. coffee, pears, apples, peanuts, vegetables and ornamental plants.

*Erysiphe graminis* (powdery mildew) on barley and wheat and other powdery mildews on various hosts such as *Sphaerotheca macularis* on hops.

*Sphaerotheca fuliginea* on cucurbits (e.g. cucumber). *Podosphaera leucotricha* on apples and *Uncinula necator* on vines.

*Helminthosporium* spp., *Rhynchosporium* spp., *Septoria* spp., *Pseudocerosporella herpotrichoides* and *Gauomannomyces graminis* on cereals.

*Cercospora arachidicola* and *Cercosporidium personata* on peanuts and other *Cercospora* species on other hosts for example sugar beet, bananas, soya beans and rice.

*Botrytis cinerea* (grey mould) on tomatoes, strawberries, vegetables, vines and other hosts.

Alternaria species on vegetables (e.g. cucumber), oil seed rape, apples, tomatoes and other hosts.

*Venturia inaequalis* (scab) on apples.

*Plasmopara viticola* on vines.

Other downy mildews such as *Bremia lactucae* on lettuce, Peronospora spp. on soybeans, tobacco, onions and other hosts and *Pseudoperonospora humuli* on hops and *Pseudoperonospora cubensis* on cucurbits.

*Phytophthora infestans* on potatoes and tomatoes and other Phytophthora spp. on vegetables, strawberries, avocado, pepper, ornamentals, tobacco, cocoa and other hosts.

*Thanatephorus cucumeris* on rice and other *Rhizoctonia* species on various hosts such as wheat and barley, vegetables, cotton and turf.

Some of the compounds have also shown a broad range of activities against fungi in vitro. They have activity against various post-harvest diseases of fruit (e.g. *Penicillium digitatum* and *italicum* and *Trichoderma viride* on oranges and *Gloesporium musarum* on bananas).

Further some of the compounds are active as seed dressings against Fusarium spp., Septoria spp., Tilletia spp. (bunt, a seed borne disease of wheat), Ustilago spp., *Helminthosporium* spp. on cereals, *Rhizoctonia solani* on cotton and *Pyricularia oryzae* on rice.

The compounds can move acropetlaly in the plant tissue. Moreover, the compounds can be volatile enough to be active in the vapour phase against fungi on the plant.

The compounds may also be useful as industrial (as opposed to agricultural) fungicides, e.g. in the prevention of fungal attack on wood, hides, leather and especially paint films.

Some of the compounds exhibit herbicidal activity and at the appropriately higher rate of application may be used to combat weeds.

Similarly, some compounds exhibit plant growth regulating activity and may be deployed for this purpose, again at appropriate rates of application.

This invention, therefore, includes the foregoing uses of the compounds (and compositions containing them) in addition to their principal use as fungicides.

The compounds may be used as such for fungicidal purposes but are more conveniently formulated into compositions for such usage. The invention thus provides a fungicidal composition comprising a compound of general formula (I) as hereinbefore defined, or a metal complex thereof; and, optionally, a carrier or diluent.

The invention also provides a method of combating fungi, which comprises applying to a plant, to seed of a plant, or to the locus of the plant or seed, a compound or metal complex thereof, as hereinbefore defined.

The compounds and metal complexes of the invention can be applied in a number of ways. For example they can be applied, formulated or unformulated, directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as a vapour; or as slow release granules. Application can be to any part of the plant, bush or tree, for example to the foliage, stems branches or roots, or to soil surrounding the roots, or to the seed before it is planted; or to the soil generally, to paddy water or to hyroponic culture systems. The invention compounds may also be injected into plants or trees and they may also be sprayed onto vegetation using electrodynamic spraying techniques, or other low volume methods.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g. 2-ethoxyethanol and 2-butoxyethanol).

The compositions to be used as sprays may also be in the form of aerosols wherein the formulation is held in a container under pressure in the presence of a propellant, e.g. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The compounds can be used as mixtures with fertilizers (e.g. nitrogen-, potassium- or phosphorus-containing fertilizers). Compositions comprising only granules of fertiliser incorporating, for example coated with, the compound are preferred. Such granules suitably contain up to 25% by weight of the compound. The invention therefore also provides a fertiliser composition comprising the compound of general formula (I) or metal complex thereof.

The compositions may also be in the form of liquid preparations for use as dips or sprays which are generally aqueous dispersions or emulsions containing the active ingredient in the presence of one or more surfactants e.g. wetting agent(s), dispersing agent(s), emulsifying agent(s) or suspending agent(s); or which are spray formulations of the kind suitable for use in electrodynamic spraying techniques. The foregoing agents can be cationic, anionic or non-ionic agents. Suitable cationic agents are quaternary ammonium compounds, for example cetyltrimethylammonium bromide.

Suitable anionic agents are soaps, salts of aliphatic monesters of sulphuric acid (for example sodium lauryl sulphate), and salts of sulphonated aromatic compounds (for example sodium dodecylbenzenesulphonate, sodium, calcium or ammonium lignosulphonate, butyl-naphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), and the concentrate is to be diluted with water before use. These concentrates often should be able to withstand storage for prolonged periods and after such storage be capable of dilution with water in order to form aqueous preparations which remain homogeneous for a sufficient time to enable them to be applied by conventional and electrodynamic spray equipment. The concentrates may conveniently contain up to 95%, suitably 10-85%, for example 25-60%, by weight of the active ingredient(s). These concentrates suitably contain organic acids (e.g. alkaryl or aryl sulphonic acids such as xylenesulphonic acid or dodecyl benzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, e.g. compounds having similar or complementary fungicidal activity or compounds having plant growth regulating, herbicidal or insecticidal activity.

The other fungicidal compound can be, for example, one which is capable of combating ear diseases of cereals (e.g. wheat), such as Septoria, Gibberella and Helminthosporium spp., seed and soil borne diseases seed downy and powdery mildews on grapes and powdery mildew and scab on apple etc. These mixtures of fungicides can have a broader spectrum of activity than the compound of general formula (I) alone; further, the other fungicide can have a synergistic effect on the fungicidal activity of the compound of general formula (I). Examples of the other fungicidal compounds are carbendazim, benomyl, thiophanate-methyl, thiabendazole, fuberidazole, etridazole, dichlofluanid, cymoxanil, oxadixyl, ofurace, metalaxyl, furalaxyl, benalaxyl, fosetyl aluminium, fenarimol, iprodione, procymidione, vinclozolin, penconazole, myclobutanil, R151297, S3308, pyrazophos, ethirimol, ditalimfos, tridemorph, triforine, nuarimol, triazbutyl, guazatine, propiconazole, prochloraz, flutriafol, chlortriafol i.e. the chemical 1-(1,2,4-triazol-1-yl)-2-(2,4-dichlorophenyl)-hexan-2-ol, DPX H6573(1-((bis-4-fluorophenyl)methylsilyl)methyl)-1H-1,2,4-triazole, triadimefon, triadimenol, diclobutrazol, fenpropimorph, fenpropidine, triademorph, imazalil, fenfuram, carboxin, oxycarboxin, methfuroxam, dodemorph, BAS 454, blasticidin S, Kasugamycin, edifenphos, kitazin P, phthalide, probenazole, isoprothiolane, tricyclazole, pyroquilan, chlorobenzthiazone, neoasozin, polyoxin D, validamycin A, repronil, flutolanil, pencycuron, diclomezine, phenazin oxide, nickel diemthyldithiocarbamate, techlofthalam, bitertanol, bupirimate, etaconazole, streptomycin, cypofuram, biloxazol, quinomethionate, dimethirimol, fenapanil, tolclofos-methyl, pyroxyfur, polyram, maneb, mancozeb, captafol, chlorothalonil, aniliazine, thiram, captan, folpet, zineb, propineb, sulphur, dinocap, binapacryl, nitrothal-isopropyl, dodine, dithianon, fentin hydroxide, fentin acetate, technazene, quintozene, dichloran, copper containing compounds such as copper oxychloride, copper sulphate and Bordeaux mixture, and organomercury compounds such as 1-(2-cyano-2-methoxyiminoacetyl)-3-ethyl urea.

The compounds of general formula (I) can be mixed with soil, peat or other rooting media for the protection of plants against seed-borne, soil-borne or foliar fungal diseases.

Suitable insecticides are pirimicarb, dimethoate, demeton-s-methyl, formothion, carbaryl, isoprocarb, XMC, BPMC, carbofuran, carbosulfan, diazinon, fenthion, fenitrothion, phentoate, chlorpyrifos, isoxathion, propaphos, monocrotophas, buprofezin, ethroproxygen and cycloprothrin.

The plant growth regulating compound can be one which controls weeds or seedhead formation, or selectively controls the growth of the less desirable plants (e.g. grasses).

Examples of suitable plant growth regulating compounds, for use with the invention compounds are the gibberellins (e.g. GA$_3$, GA$_4$ or GA$_7$), the auxins (e.g. indoleacetic acid, indolebutyric acid, naphthoxyacetic acid or naphthylacetic acid), the cytokinins (e.g. kinetin, diphenylurea, benzimidazole, benzyladenine or benzylaminopurine), phenoxyacetic acids (e.g. 2,4-D or MCPA), substituted benzoic acids (e.g. triiodobenzoic acid), morphactins (e.g. chlorfluorecol), maleic hydrazide, glyphosate, glyphosine, long chain fatty alcohols and acids, dikegulac, paclobutrazol, flurprimidol, fluoridamid, mefluidide, substituted quaternary ammonium and phosphonium compounds (e.g. chlormequat, chlorphonium or mepiquatchloride), ethephon, carbetamide, methyl-3,6-dichloroanisae, daminozide, asulam, abscisic acid, isopyrimol, 1-(4-chlorophenyl)-4,6-dimethyl-2-oxo-1,2-dihydropyridine-3-carboxylic acid, hydroxybenzonitriles (e.g. bromoxynil), difenzoquat, benzoylprop-ethyl 3,6-dichloropicolinic acid, paclobutrazol, fenpentezol, inabenfide, triapenthenol and tecnazene.

The following Examples illustrates the invention. Throughout these examples, the term "ether" refers to diethyl ether, magnesium sulphate was used to dry solutions, and reactions involving water-sensitive intermediates were performed under atmospheres of nitrogen. Unless otherwise stated, chromatography was performed using silica gel as the stationary phase. Where shown, infrared and nmr data are selective; no attempt is made to list every absorption. The following abbreviations are used throughout:

| THF = tetrahydrofuran | s = singlet |
| DMF = N,N-dimethylformamide | d = doublet |
| GC = Gas chromatography | t = triplet |
| MS = Mass spectrum | m = multiplet |

EXAMPLE 1

This Example illustrates the preparation of 2E,1″Z-methyl 3-methoxy-2-[2′-(2″-phenylethenyl)phenyl]-propenoate (compound Number 13 of Table I).

Potassium tert-butoxide (5.30 g) was added in a single proton to a vigorously-stirred suspension of benzyltriphenylphosphonium chloride (21.02 g) in dry ether (250 ml). After 25 mins, the resulting orange mixture was treated with a solution of 2-bromobenzaldehyde (5.00 g) in dry ether (50 ml), and the mixture lightened in colour. After a further hour, the mixture was poured into water and extracted with ether. The extracts were washed with water, dried, concentrated under reduced pressure, and chromatographed using dichloromethane as eluent to give 1-phenyl-2-(2-bromophenyl)ethylene (5.95 g, 85% yield), an almost colourless oil, as a 6:1 mixture of Z:E-isomers (by GC/MS).

A solution of the Grignard reagent prepared from part of the mixture of isomers of 1-phenyl-2-(2-bromophenyl)ethylene described above (5.58 g) and magnesium (0.63 g) in dry THF (20 ml) was added dropwise over 30 mins. to a stirred solution of dimethyl oxalate (5.06 g) in dry THF (40 ml) cooled to −15° C. The resulting mixture was stirred at about −15° C. for 30 minutes, then at room temperature for 1 hour, then poured into dilute hydrochloric acid and extracted with ether. The extracts were washed with water, dried, concentrated under reduced pressure, then chromatographed twice [(i) 30% ether in petrol; (ii) 20% hexane in dichloromethane] to give isomerically pure Z-methyl 2-(2′-phenylethenyl)phenylglyoxalate (1.76 g, 31% yield) as a yellow oil, $^1$H nmr (CDCl$_3$) : delta 3.87 (3H, s), 6.78 (centre of 2 doublets, each 1 H, J 12Hz) p.p.m.

Potassium tert-butoxide (2.00 g) was added in a single portion to a stirred suspension of (methoxymethyl)triphenylphosphonium chloride (6.78 g) in dry ether (80 ml). After 25 minutes, the resulting red suspension was treated with a solution of Z-methyl 2-(2′-phenylethenyl)phenylglyoxalate (1.76 g) in dry ether (20 ml), the colour lightening. After 1.5 hours, the reaction mixture was poured into water and extracted with ether. The extracts were washed with water, dried, flushed through a short column of silica gel with dichloromethane, then carefully chromatographed using 30% ether in petrol as eluant to give the title compound (0.46 g, 24% yield) as an oil, infrared (film) : 1715, 1635 cm$^{-1}$; $^1$H nmr (CDCl$_3$) : delta 3.62 (3H, s), 3.73 (3H, s), 6.48 (2H, s), 7.50 (1H, s ppm.

EXAMPLE 2

This Example illustrates the preparation of E- and Z-methyl 3-methoxy-2-phenylpropenoate (compounds number 1 and 2 of Table I).

Potassium tert-butoxide (9.52 g) was added in a single portion to a stirred suspension of methoxymethyl)triphenylphosphonium chloride (34.3 g) in dry ether (300 ml). After 45 minutes, the resulting red suspension was treated with a solution of methyl benzoylformate (8.20 g) in dry ether (100 ml) (colour lightens; exotherm). After 3 hours, the mixture was diluted with water, treated with magnesium sulphate and charcoal, then concentrated under reduced pressure to give the crude product (36.39 g) as a yellow oil which partially crystallised on standing. This was flushed through silica gel using dichloromethane then carefully chromatographed using dichloromethane: petrol (2:1) to give E-methyl 3-methoxy-2-henylpropenoate (4.83 g, 50% yield) as a yellow oil, eluted first, infrared (film ): 1710, 1630 cm$^{-1}$, $^1$H nmr (CDCl$_3$) : delta 7.55 (s, olefinic proton), and Z-methyl 3-methoxy-2-phenylpropenoate (3.43 g, 36% yield) as a pale yellow oil, eluted second, infrared (film) : 1715, 1630 cm$^{-1}$, $^1$H nmr (CDCl$_3$) : delta 3.76 (3H, s), 3.90 (3H, s), 6.65 (1H, s), 7.28 (5H, s) ppm.

A sample of E-methyl 3-methoxy-2-phenylpropenoate prepared from methyl phenylacetate by the method described in Examples 4 and 7, that is by reaction with sodium hydride and methyl formate and treatment of the resulting enol with potassium carbonate and dimethyl sulphate, solidified on standing and had a melting point of 37°-38° C.

EXAMPLE 3

This Example illustrates the preparation of 2E-, 1"E- and 2Z,1"E-methyl 3-methoxy-2-[2'-(2"-phenylethenyl)phenyl]propenoate (compounds numbers 9 and 10 of Table I).

A solution of 2-bromobenzaldehyde (18.50 g) in dry ether (20 ml ) was added dropwise to a stirred solution of benzylmagnesium chloride [prepared from benzyl chloride (12.64 g) and magnesium (2.68 g)] in dry ether (120 ml), a thick precipitate forming during the addition. The mixture was stirred for 1 hour at room temperature then poured into water, acidified with 2M hydrochloric acid, and extracted with ether. The extracts were washed with water, dried, concentrated and chromatographed using dichloromethane and petrol (1:1) as eluant to give 1-(2-bromophenyl)-2-phenylethan-1-ol (10.95 g, 40%) as a white solid, melting point 84°-85° C.

A stirred mixture of 1-(2-bromophenyl)-2-phenylethan-1-ol (15.50 g) and orthophosphoric acid (150 ml) was heated at 170° C. for 1 hour and then poured into iced water and extracted with ether. The extracts were washed with water, dried and concentrated to give the crude product as an orange oil (14.29 g). Evaporative distillation (0.3 torr; oven temperature 140° C.) gave E-1-phenyl-2-(2-bromophenyl)ethylene (12.53 g, 86% yield) as a pale yellow oil with a purity of 97% by GC.

A solution of the Grignard reagent prepared from E-1-phenyl-2-(2 -bromophenyl)ethylene (8.56 g) and magnesium (0.96 g) in dry tetrahydrofuran (20 ml) was added dropwise over 30 minutes to a stirred solution of dimethyl oxalate (7.76 g) in dry tetrahydrofuran (70 ml) cooled to −15° C. The resulting mixture was stirred at about −15° C. for 30 minutes, then at room temperature for 1 hour, then poured into dilute hydrochloric acid and extracted with ether. The extracts were washed with water, dried and concentrated to give the crude product as a pale yellow oil (17.22 g). Purification by column chromatography using dichloromethane and petrol (1:1) as eluant then evaporative distillation (0.07 torr, oven temperature 170° C.) gave E-methyl 2-(2'-phenylethenyl)phenylglyoxalate (2.01 g, 23% yield) as a yellow oil, pure by GC, $^1$H nmr (CDCl$_3$) : delta 3.78 (3H, s), 6.88 (centre of 2 doublets, each 1 H, J 16Hz) p.p.m.

Potassium tert-butoxide (2.19 g) was added in a single portion to a stirred suspension of (methoxymethyl)triphenylphosphonium chloride (7.41 g) in dry ether (100 ml). After 25 minutes, the resulting red suspension was treated with a solution of E-methyl 2-(2'-phenylethenyl)phenylglyoxalate (1.92 g) in dry ether (20 ml), the colour lightening. After 15 minutes, the mixture was poured into with water and extracted with ether. The extracts were washed with water, dried and chromatographed using 30% ether in petrol as eluant to give (i) the 2E,1"E-isomer of the title compound, eluted first, as a pale yellow oil (1.06 g, 50% yield) which crystallised on standing to give a white solid, melting point 103°-104° C. An analytical sample, recrystallized from an ether-petrol mixture, had melting point 107°-108° C., infrared (nujol mull): 1700, 1630 cm$^{-1}$; $^1$H nmr (CDCl$_3$) : delta 3.68 (3H, s), 3.80 (3H, s), 7.06 (2H, s), 7.63 (1H, s) p.p.m; and (ii) the 2Z,1"E-isomer of the title compound, eluted second, as a viscous oil (0.260 g, 12% yield) infrared (film) : 1710, 1625 cm$^{-1}$; $^1$H nmr (CDCl$_3$) : delta 3.65 (3H, s), 3.92 (3H, s), 6.57 (1H, s), 6.99 and 7.24 (each 1H, d J 16Hz) ppm.

EXAMPLE 4

This Example illustrates the preparation of E-methyl 2-(2-chloro-6-fluorophenyl)-3-methoxypropenoate (compound No. 27 of Table I).

A mixture of methyl (2-chloro-6-fluorophenyl)acetate (5.20 g) and methyl formate (31.4 ml) in dry DMF (40 ml) was added dropwise to a stirred suspension of sodium hydride (1.23 g) in dry DMF (40 ml) at a temperature between 0° and 5° C. Vigorous evolution of gas was observed. The reaction mixture was stirred at room temperature for 3.5 hours, then poured into a mixture of ice and aqueous sodium carbonate, and washed with ether. The resulting aqueous mixture was acidified with concentrated hydrochloric acid and extracted with ether. The extracts were washed with water, dried and concentrated to give methyl 2-(2-chloro-6-fluorophenyl)-3-hydroxypropenoate (3.44 g) as a white solid.

A stirred solution of this crude product in dry DMF (30 ml) was treated successively with potassium carbonate (4.11 g) and dimethyl sulphate (1.34 ml). The resulting mixture was stirred at room temperature for 1 hour, and was then poured into water and extracted with ether. The extracts were washed with water, dried and concentrated to give the title compound (2.91 g) as a white solid, melting point 77°-78° C. Crystallisation from 60°-80° petrol gave colourless crystals [2.61 g, 42% yield from methyl (2-chloro-6-fluorophenyl)-acetate], melting point 79°-80°, $^1$NMR (CDCl$_3$) delta 3.69 (3H, s), 3.84 (3H, s), 7.62 (1H, s) ppm.

EXAMPLE 5

This Example illustrates the preparation of E-methyl 2-(2-phenoxy)phenyl-3-methoxyacrylate (compound number 1 of Table II).

Potassium tert-butoxide (5.6 g) was added to a stirred solution of diphenyl ether (12.3 g) in dry ether (150 ml) at −70° C. The resulting mixture was stirred at this temperature for 15 minutes, then n-butyl-lithium (30.5 ml of 1.62M solution in hexane) was added to give a red-brown suspension which was allowed to warm to room temperature. This mixture was added to a stirred suspension of dimethyl oxalate (11.8 g) in ether (250 ml) at −10° C. over 20 minutes, then allowed to warm to room temperature. After 30 minutes, the mixture was poured into water and extracted with ether. The combined extracts were washed with water, dried, then concentrated to give a red oil (14.21 g). Chromatography using 20% ether in petrol as eluant gave methyl 2-phenoxyenzoylformate (2.23 g) as a yellow oil.

Potassium tert-butoxide (2.64 g) was added to a vigorously stirred suspension of (methoxymethyl)triphenylphosphonium chloride (8.93 g) in dry ether (100 ml). After 20 minutes, the resulting red suspension was treated with a solution of methyl 2-phenoxybenzoylformate (2.23 g) in dry ether (20 ml), the color lightening. After 15 minutes, the mixture was poured into water and extracted with ether. The combined extracts were washed with water, dried, and concentrated to give a yellow oil (7.30 g). Chromatography using dichloromethane as eluant gave the title compound (0.61 g) as colourless oil, infrared (film) 1 710, 1 635 cm$^{-1}$, $^1$nmr (CDCl$_3$) delta 3.60 (3H, s), 3.75 (3H, s), 7.47 (1H, s) ppm.

EXAMPLE 6

This Example describes an alternative method for the preparation of E-methyl 2-(2-phenoxy)phenyl-3-methoxypropenoate (compound number 1 of Table II).

A 1M solution of borane-tetrahydrofuran complex (30 ml) was added dropwise to a stirred solution of 2-phenoxybenzoic acid (5.35 g) in dry THF (50 ml), cooled to 0° C. (effervescence). Following the addition, the mixture was stirred at 0° C. for 15 minutes, then at room temperature for 1.5 hours. It was poured into water and extracted with ether. The extracts were washed successively with water, aqueous sodium bicarbonate, aqueous sodium carbonate, then dried and concentrated under reduced pressure to give 2-phenoxybenzyl alcohol (4.83 g, 97%) as a colourless oil.

Thionyl chloride (1.92 ml) was added in one portion to a solution of 2-phenoxybenzyl alcohol (4.80 g) in dry dichloromethane (50 ml). The resulting mixture was stirred at room temperature for 2 hours, then washed with water (×2), aqueous sodium bicarbonate (×2) and aqueous sodium chloride, dried and concentrated under reduced pressure to give 2-phenoxybenzyl chloride (4.87 g, 93%) as a colourless oil.

Carbon dioxide was bubbled into a solution of 2-phenoxybenzylmagnesium chloride [from 2-phenoxybenzyl chloride (4.80 g) and magnesium turnings (0.64 g)] in dry ether (15 ml), cooled to 0° C. Dry THF was added to aid solubility. When exothermic reaction had subsided, no further carbon dioxide was passed through the mixture and it was allowed to warm to room temperature. The mixture was poured into water, washed with ether, then treated with hydrochloric acid and extracted with ether. The extracts were washed with water, dried and concentrated under reduced pressure to give 2-phenoxyphenylacetic acid (3.06 g, 61%) as a solid, melting point 82°-85° C. An analytic sample, recrystallised from ether/petrol, had a melting point of 85°-86° C.

A solution of 2-phenoxyphenylacetic acid (2.75 g) in dry methanol (30 ml) containing concentrated sulphuric acid (0.3 ml) was heated under reflux for 2 hours then allowed to cool, poured into water and extracted with ether. The extracts were washed with water, dried and concentrated under reduced pressure to give methyl 2-phenoxyphenylacetic (2.65 g, 91%) as a pale yellow oil.

This ether was converted in 2 steps into the title compound by the method described in Example 4, that is, by reaction with sodium hydride and methyl formate and treatment of the resulting enol with potassium carbonate and dimethyl sulphate (overall yield=65%).

EXAMPLE 7

This Example illustrates the preparation of E-methyl 2-(2-benzyloxy)phenyl-3-methoxyacrylate (compound number 177 of Table II).

A mixture of methyl formate (24.4 ml) and methyl o-(benzyloxy)phenylacetate (5.10 g) in dry THF (30 ml) was added dropwise to a stirred suspension of sodium hydride (0.95 g) in dry DMF (30 ml) at between 0° and 5° C. A vigorous evolution of gas was observed. The reaction mixture was stirred at room temperature for 3.5 hours, then poured into a mixture of ice and aqueous sodium bicarbonate. The resulting aqueous solution was washed with ether (×3) then acidified with concentrated hydrochloric acid and extracted with ether. The extracts were washed with water, dried and concentrated to give methyl 2-(2-benzyloxy)phenyl-3-hydroxyarylate (4.38 g) as a yellow oil.

Potassium carbonate (4.26 g) and dimethyl sulphate (1.38 ml) were added successively to a stirred solution of methyl 2-(2-benzyloxy)phenyl-3-hydroxyarylate (4.38 g) in dry DMF (40 ml). After an hour at room temperature, the reaction mixture was poured into water and extracted with ether. The extracts were washed with water, dried, concentrated and triturated with petrol to give the tile compound (3.38 g, 57% yield from methyl o-(benzyloxy)phenylacetate) as a white solid, melting point 74°-75° C. Crystallisation of the whole sample from methanol gave colourless crystals (2.35 g), melting point 76°-77°, $^1$H nmr (CDCl$_3$) delta 3.63 (3H, s), 3.76 (3H, s), 5.05 (2H, s), 7.49 (1H, s) ppm.

EXAMPLE 8

This Example describes the preparation of E-methyl 2-(4-chlorophenyl)-3-methoxypropenoate (compound number 22 of Table I).

A solution of methyl 4-chlorophenylacetate (3.51 g) in dry THF (25 ml) was added dropwise to a stirred solution of lithium di-isopropylamide [from di-isopropylamine (2.88 g) and n-butyl-lithium (16.4 ml of 1.62M solution in n-hexane)] in dry DMF (25 ml) at −70° C. After 0.5 hours at the same temperature, a solution of trimethylsilyl chloride (5.16 g) in dry THF (5 ml) was added and after 10 minutes the solution was allowed to warm to room temperature. Volatile components of the resulting mixture were removed under reduced pressure, and the ether-soluble fraction of the residue was collected by repeated trituration with dry ether, filtering, and concentrating the filtrate under reduced pressure. This left the crude methyl silyl enol ether (5.18 g) as an orange oil whose infrared spectrum showed almost no carbonyl absorption and a peak at 1 640 cm$^{-1}$.

A solution of titanium tetrachloride (3.60 g) in dry dichloromethane (5 ml) was added dropwise to a stirred solution of trimethylorthoformate (1.92 g) in dry dichloromethane (30 ml) at −70° C. After 15 minutes at the same temperature, a solution of the crude methyl silyl enol ether described above (5.18 g) in dry dichloromethane (20 ml) was added, still at −70° C. After 0.5 hours, aqueous potassium carbonate was added to the reaction mixture, still at −70° C., and it was extracted with ether. The extracts were washed with water, dried, concentrated under reduced pressure, and chromatographed using ether : petrol (1:1) as eluant to give methyl 2-(4-chlorophenyl)-3,3-dimethoxypropoante (2.26 g, 46% yield from methyl 4-chlorophenyl acetate) as a solid, melting point 61°-62° C.

A solution of methyl 2-(4-chlorophenyl)-3,3-dimethoxypropoante (1.65 g) in dry THF (20 ml) was added dropwise at −70° C. to a stirred solution of lithium di-isopropylamide [from di-isopropylamine (0.84 g) and n-butyl-lithium (4.7 ml of 1.62M solution in n-hexane)] in dry TMF (20 ml). After 0.5 hours at −70° C., the reaction mixture was poured into water and extracted with ether. The extracts were washed with water, dried, and concentrated under reduced pressure, and chromatographed using 40% ether in petrol as eluant to give the tile compound (0.31 g, 21%) as a pale yellow solid, melting point 61°-62° C., infrared (nujol) 1 685, 1 615 cm$^{-1}$, $^1$H nmr (CDCl$_3$) delta 3.74 and 3.88 (each (3H, s), 7.56 (1H, s) ppm.

EXAMPLE 9

This Example describes the preparation of E-methyl 2-(4-methoxyphenoxy)]phenyl)-3-methoxypropenoate (compound number 16 of Table II).

4-Methylphenol (8.40 g) was added dropwise to a stirred methanolic solution of sodium methoxide [from sodium (1.78 g) and dry methanol (50 ml)]. After 0.5 hours, the methanol was removed under reduced pressure and the residue was mixed with 4-methylphenol (4.20 g), 2-chloroacetophenone (6.00 g), and a catalytic quantity of copper bronze. The resulting mixture was heated at 135° C. for 1.5 hours, then allowed to cool, diluted with water and extracted with ether. The extracts were washed successively with aqueous sodium hydroxide and aqueous sodium chloride, then dried and concentrated under reduced pressure to give a dark oil (8.20 g). This crude produce was purified by evaporative distillation (130°-135° C. at 0.02 torr) to give 2-(4-methylphenoxy)acetophenone (7.29 g, 83%) as a colourless liquid, infrared (film) 1 670 cm$^{-1}$.

A solution of boron trifluoride etherate (18.06 g) and 2-4-(methylphenoxy)acetophenone (7.29 g) in dry methanol (8.3 ml) was added to a stirred ice-cooled suspension of lead tetra-acetate (14.97 g) in dry ether (70 ml). The resulting mixture was stirred at room temperature for 18 hours, then poured into water and extracted with ether. The extracts were washed successively with water and aqueous sodium bicarbonate, dried and concentrated under reduced pressure to give a red oil (7.53 g) containing methyl 2-4-(methylphenoxy)phenylacetate and the starting acetophenone (4:1 by GC). The mixture was treated with aqueous potassium hydroxide, and the resulting substituted phenylacetic acid was purified by acid-base extractions, and re-esterified in acidic methanol to give methyl 2-(4-methylphenoxy)phenylacetate (5.00 g) as a thick oil, infrared (film) 1 730 cm$^{-1}$.

This ester was converted in 2 steps into the title compound by the method described in Examples 4 and 7, that is, by reaction with sodium hydride and methyl formate and treatment of the resulting enol with potassium carbonate and dimethyl sulphate (overall yield=32%). The product, after recrystallisation from methanol, had a melting point of 80°-81° C., infrared (nujol) 1 690, 1 620 cm$^{-1}$, $^1$H nmr (CDCl$_3$) delta 2.30 (3H, s), 3.62 (3H, s), 3.77 (3H, s), 7.50 (1H, s) ppm.

EXAMPLE 10

This Example describes the preparation of E- and Z-methyl 3-methoxy-2-(2-phenylethyl)phenylpropenoate (compounds numbers 1 and 177 of Table IV).

Trifluoroacetic acid (46 ml) was added in one portion to a stirred mixture of 1-(2-bromophenyl)-2-phenylethan-1-ol (16.51 g, prepared as described in Example 3) and triethylsilane (13.80 g). The resulting mixture was stirred at room temperature for about 22 hours, then the excess trifluoroacetic acid was removed under reduced pressure. The residue was dissolved in ether and washed successively with water, aqueous sodium bicarbonate (×3) and water (×2), then dried, concentrated under reduced pressure, and chromatographed using 10% dichloromethane in petrol as eluant to give 1-(2-bromophenyl)-2-phenylethane (8.02 g, 52%) as a colourless oil.

This sample of 1-(2-bromophenyl)-2-phenylethane was converted in 2 steps into the title compounds by the method described in Examples 1 and 3, that is, by reaction of the magnesium derivative with dimethyl oxalate, and treatment of the resulting ketoester with methoxymethylenetriphenylphosphorane. The E-isomer, eluted first in 30% ether in petrol, was an oil, infrared (film) 1 705 and 1 630 cm$^{-1}$, $^1$H nmr (CDCl$_3$) delta 2.79

(4H, s), 3.69 (3H, s), 3.79 (3H, s), 7.59 (1H, s) ppm. The Z-isomer, eluted second, was also an oil, infrared (film) 1 715, 1 695 and 1 630 cm$^{-1}$, $^1$H nmr (CDCl$_3$) delta 2.84 (4H, s), 3.68 (3H, s), 3.84 (3H, s), 6.24 (1H, s) ppm.

EXAMPLE 11

This Example illustrates the preparation of 2E, 1″E- and 2Z, 1″E-methyl 2-[2′-(2″-[2‴-furyl]ethenyl)-phenyl]-3-methoxypropenoate (compounds numbers 55 and 56 of Table I).

A mixture of 2-bromobenzyl bromide (12.10 g) and trimethylphosphite (8.56 ml) was stirred in a flask fitted via a still head to a condenser. This reaction mixture was heated at 110° C. for 1 hour [then further trimethylphosphite (5 ml) was added] then at 130° C. for 2.5 hours, the temperature at the still head remaining at leas then 40° C. throughout. The mixture was allowed to cool, and the volatile fraction was removed under reduced pressure to leave an almost colourless liquid (21.65 g). Evaporative distillation of part of this liquid (18.35 g) gave dimethyl 2-bromobenzylphosphonate (8.02 g, 55%) was a colourless liquid, collected at 175°-180° C. (0.15 mbar), with a purity of 78% by GC. An analytical sample, purified by chromatography using ethyl acetate : 60°-80° C. petrol (2:1) as eluant, had $^1$H nmr (CDCl$_3$) delta 3.43 (2H, d J 23 Hz), 3.72 (d J 11 Hz) ppm.

A solution of dimethyl 2-bromobenzylphosphonate (10.35 g) in dry DMF (50 ml) was added dropwise at room temperature to a stirred suspension of sodium hydride (0.979 g) in dry DMF (100 ml) (effervescence). After 20 minutes, a solution of furfural (3.56 g) in dry DMF (50 ml) was added (exotherm) and the resulting mixture was stirred at room temperature for 4 hours, then diluted with water and extracted with ether. The extracts were washed with water, treated with magnesium sulphate and charcoal, filtered, concentrated under reduced pressure, and chromatographed using 40°-60° C. petrol as eluant to give E-1-(2-furyl)-2-(2-bromophenyl)-ethylene (3.755 g), a pale yellow liquid (containing about 6% of the corresponding Z-isomer by GC).

This ethylene was converted in 2 steps into the title compounds by the method described in Examples 1 and 3, that is, by reaction of the magnesium derivative with dimethyl oxalate, and treatment of the resulting keto-ester with methoxymethylenetriphenylphosphorane. The E,E-isomer, eluted first in 30% ether in petrol, was an oil, infrared (film) 1 715 and 1 637 cm$^{-1}$, $^1$H nmr (CDCl$_3$) delta 3.68 (3H, s), 3.81 (3H, s), 6.31 (1H,d J 3.5 Hz), 6.40 (1H, dd J 3.5 and 2 Hz), 6.83 and 6.98 (each 1H, d J 16Hz), 7.63 (1H, s) ppm; the Z,E-isomer was a solid, melting point 107.5°-110° C., infrared (nujol) 1 717 and 1 625 cm$^{-1}$, $^1$H nmr (CDCl$_3$) delta 3.65 (3H,s), 3.93 (3H,s), 6.33 (1H, d J 3.5 Hz), 6.40 (1H,dd J 3.5 and 2 Hz), 6.56 (1H,s), 6.82 and 7.1 (each 1H, d J 16Hz) ppm.

EXAMPLE 12

An emulsifiable concentrate was made up by mixing the ingredients, and stirring the mixture until all the constituents were dissolved.

| | |
|---|---|
| Compound of Example 5 | 10% |
| Ethylene dichloride | 40% |
| Calcium dodecylbenzenesulphate | 5% |
| "Lubrol" L | 10% |
| "Aromasol" H | 35% |

EXAMPLE 13

A composition in the form of grains readily dispersible in a liquid, e.g. water, was prepared by grinding together the first three ingredients in the presence of added water and then mixing in the sodium acetate. The resultant mixture was dried and passed Z-isomer by GC).

This ethylene was converted in 2 steps into the title compounds by the method described in Examples 1 and 3, that is, by reaction of the magnesium derivative with dimethyl oxalate, and treatment of the resulting keto-ester with methoxymethylenetriphenylphosphorane. The E,E-isomer, eluted first in 30% ether in petrol, was an oil, infrared (film) 1 715 and 1 637 cm$^{-1}$, $^1$H nmr (CDCl$_3$) delta 3.68 (3H, s), 3.81 (3H, s), 6.31 (1H,d J 3.5 Hz), 6.40 (1H, dd J 3.5 and 2 Hz), 6.83 and 6.98 (each 1H, d J 16Hz), 7.63 (1H, s) ppm; the Z,E-isomer was a solid, melting point 107.5°-110° C., infrared (nujol) 1 717 and 1 625 cm$^{-1}$, $^1$H nmr (CDCl$_3$) delta 3.65 (3H,s), 3.93 (3H,s), 6.33 (1H, d J 3.5 Hz), 6.40 (1H,dd J 3.5 and 2 Hz), 6.56 (1H,s), 6.82 and 7.1 (each 1H, d J 16Hz) ppm.

EXAMPLE 12

An emulsifiable concentrate was made up by mixing the ingredients, and stirring the mixture until all the constituents were dissolved.

| | |
|---|---|
| Compound of Example 5 | 10% |
| Ethylene dichloride | 40% |
| Calcium dodecylbenzenesulphate | 5% |
| "Lubrol" L | 10% |
| "Aromasol" H | 35% |

EXAMPLE 13

A composition in the form of grains readily dispersible in a liquid, e.g. water, was prepared by grinding together the first three ingredients in the presence of added water and then mixing in the sodium acetate. The resultant mixture was dried and passed through a British Standard mesh sieve, size 44-100, to obtain the desired size of grains.

| | |
|---|---|
| Compound of Example 3 | 50% |
| "Dispersol" T | 25% |
| "Lubrol" APN5 | 1.5% |
| Sodium acetate | 23.5% |

EXAMPLE 14

The ingredients were all ground together to produce a powder formulation readily dispersible in liquids.

| | |
|---|---|
| Compound of Example 5 | 45% |

| | |
|---|---|
| "Dispersol" T | 5% |
| "Lissapol" NX | 0.5% |
| "Cellofas" B600 | 2% |
| Sodium acetate | 47.5% |

EXAMPLE 15

The active ingredient was dissolved in a solvent and the resultant liquid was sprayed on to the granules of China clay. The solvent was then allowed to evaporate to produce a granular composition.

| | |
|---|---|
| Compound of Example 3 | 5% |
| China clay granules | 95% |

EXAMPLE 16

A composition suitable for use as a seed dressing was prepared by mixing the three ingredients.

| | |
|---|---|
| Compound of Example 5 | 50% |
| Mineral oil | 2% |
| China clay | 48% |

EXAMPLE 17

A dusting powder was prepared by mixing the active ingredient with talc.

| | |
|---|---|
| Compound of Example 3 | 5% |
| Talc | 95% |

EXAMPLE 18

A Col formulation was prepared by ball-milling the constituents set out below and then forming an aqueous suspension of the ground mixture with water.

| | |
|---|---|
| Compound of Example 5 | 40% |
| "Dispersol" T | 10% |
| "Lubrol" APN5 | 1% |
| Water | |

EXAMPLE 19

A dispersible powder formulation was made by mixing together the ingredients set out below and then grinding the mixture until all were thoroughly mixed.

| | |
|---|---|
| Compound of Example 3 | 25% |
| "Aerosol" OT/B | 2% |
| "Dispersol" A.C. | 5% |
| China clay | 28% |
| Silica | 40% |

EXAMPLE 20

This Example illustrates the preparation of a dispersible powder formulation. The ingredients were mixed and the mixture then ground in a comminution mill.

| | |
|---|---|
| Compound of Example 5 | 25% |
| "Perminal" BX | 1% |
| "Dispersol" T | 5% |
| Polyvinylpyrrolidone | 10% |
| Silica | 25% |
| China clay | 34% |

EXAMPLE 21

The ingredients set out below were formulated into a dispersible powder by mixing then grinding the ingredients.

| | |
|---|---|
| Compound of Example 3 | 25% |
| "Aerosol" OT/B | 2% |
| "Dispersol" A | 5% |
| China clay | 68% |

In Examples 12 to 21 the proportions of the ingredients given are by weight.

The compounds set out in Tables I, II, III, IV and V are similarly formulated as specifically described in Examples 12 to 21.

There now follows an explanation of the compositions or substances represented by the various Trade Marks and Trade Names mentioned above.

LUBROL L: a condensate of nonyl phenol 1 mole) with ethylene oxide (13 moles)

AROMASOL H: a solvent mixture of alkylbenzenes

DISPERSOL T & AC: a mixture of sodium sulphate and a condensate of formaldehyde with sodium naphthalene sulphonate LUBROL APN5: a condensate of nonyl phenol (1 mole) with naphthalene oxide (5.5 moles)

CELLOFAS B600: a sodium carboxymethyl cellulose thickener

LISSAPOL NX: a condensate of nonyl phenol (1 mole) with ethylene oxide (8 moles)

AEROSOL OT/B: dioctyl sodium sulphosuccinate

PERMINAL BX: a sodium alkyl naphthalene sulphonate

EXAMPLE 22

The compounds were tested against a variety of foliar fungal diseases of plants. The technique employed was as follows.

The plants were grown in John Innes Potting Compost (No 1 or 2) in 4 cm diameter minipots. The test compounds were formulated wither by bead milling with aqueous Dispersol T or as a solution in acetone or acetone/ethanol which was diluted to the required concentration immediately before use. For the foliage diseases, the formulations (100 ppm active ingredient) were sprayed on to the foliage and applied to the roots of the plants in the soil. The sprays were applied to maximum retention and the root drenches to a final concentration equivalent to approximately 40 ppm a.i./dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:
4 = no disease
3 = trace-5% of disease on untreated plants
2 = 6-25% of disease on untreated plants
1 = 26-59% of disease on untreated plants
0 = 60-100% of disease on untreated plants The results are shown in Tables VII, VIII and IX.

TABLE VII

Data in this Table refer to compounds listed in Table I

| COMPOUND NUMBER | PUCCINIA RECONDITA (WHEAT) | ERYSIPHE GRAMINIS HORDEI (BARLEY) | VENTURIA INAEQUALIS (APPLES) | PYRICULARIA ORYZAE (RICE) | CERCOSPORA ARACHIDICOLA (PEANUT) | PLASMOPARA VITICOLA (VINES) |
|---|---|---|---|---|---|---|
| 1 | 4 | 4 | 4 | 0 | 2 | 4 |
| 2 | 2 | 0 | 0 | 0 | 0 | 0 |
| 3 | 0 | 0 | 0 | 0 | 0 | 4 |
| 4 | 0 | 0 | 1 | 0 | 0 | 0 |
| 5 | 0 | 0 | 0 | 0 | 0 | 1 |
| 7 | 0 | 0 | 1 | 0 | 0 | 0 |
| 9 | 4 | 4 | 4 | 3* | 4 | 4 |
| 10 | 4 | 4 | 4 | 3* | 4 | 4 |
| 11 | 0 | 0 | 0 | 0 | 0 | 3 |
| 12 | 0 | 0 | 0 | 0 | 0 | 2 |
| 13 | 4 | 2 | 4 | 2 | 4 | 4 |
| 14 | 4 | 4 | 4 | 4 | 4 | 4 |
| 19 | 4 | 4 | 4 | 3 | 0 | 4 |
| 20 | 0 | 2 | 4 | 3 | 3 | 4 |
| 21 | 0 | 4 | 0 | 0 | 4 | 4 |
| 22 | 0 | 0 | 0 | 0 | 0 | 4 |
| 23 | 4 | 0 | 0 | 0 | 4 | 4 |
| 24 | 4 | 2 | 4 | 0 | 0 | 4 |
| 25 | 2 | 0 | 0 | 0 | — | 3 |
| 26 | 1 | 0 | — | 0 | — | 1 |
| 27 | 3 | 2 | 4 | 2 | 2 | 4 |
| 28 | 3 | 4 | 4 | 3 | 4 | 4 |
| 29 | 2 | 3 | 4 | 0 | 0 | 3 |
| 30 | 4 | 4 | 4 | 3 | 3 | 4 |
| 31 | 0 | 4 | 2 | 0 | 0 | 3 |
| 32 | 3 | 0 | 3 | 1 | 3 | 0 |
| 35 | 0 | 2 | 0 | 2 | 4 | 0 |
| 40 | 4 | 4 | 4 | 4 | 4 | 4 |
| 42 | 3 | 4 | 4 | 4 | 1 | 4 |
| 52 | 4 | 1 | 4 | 4 | 3 | 4 |
| 53 | 0 | 0 | 4 | 0 | 2 | 4 |
| 54 | 0 | 0 | — | 0 | — | 0 |
| 55 | 0 | 0* | 4 | 3 | 1* | 4* |
| 56 | 4 | 0* | 4 | 4 | 0* | 4* |
| 57 | 3 | 0 | — | 4 | — | 0 |
| 58 | 0 | 0 | 0 | 0 | — | 3 |
| 60 | 4 | 3 | 4 | 4 | 4 | 4 |
| 61 | 3 | 0 | 2 | 2 | — | 4 |
| 66 | 0 | 3 | 0 | 0 | — | 0 |

* = tested as a foliar spray at 25 ppm

TABLE VIII

Data in this Table refer to compounds listed in Table II

| COMPOUND NUMBER | PUCCINIA RECONDITA (WHEAT) | ERYSIPHE GRAMINIS HORDEI (BARLEY) | VENTURIA INAEQUALIS (APPLES) | PYRICULARIA ORYZAE (RICE) | CERCOSPORA ARACHIDICOLA (PEANUT) | PLASMOPARA VITICOLA (VINES) |
|---|---|---|---|---|---|---|
| 1 | 4 | 4 | 4 | 3 | 4 | 4 |
| 7 | 4 | 4 | 4 | 4 | 4 | 4 |
| 66 | 3 | 4 | 4 | 0 | 0 | 3 |
| 153 | 4 | 4 | 4 | 0 | 3 | 4 |
| 160 | 0 | 4 | 4 | 3 | 4 | 4 |
| 161 | 0 | 0 | 4 | 0 | 3* | 3 |
| 177 | 4 | 4 | 4 | 2 | 4 | 4 |
| 180 | 0 | 0 | 0 | 0 | 0 | 3 |
| 181 | 4* | 0* | 4* | 0* | 0* | 0* |

* = tested as foliar spray at 25 ppm

TABLE IX

| | Data in this Table refer to compounds listed in Table IV | | | | | |
|---|---|---|---|---|---|---|
| COMPOUND NUMBER | PUCCINIA RECONDITA (WHEAT) | ERYSIPHE GRAMINIS HORDEI (BARLEY) | VENTURIA INAEQUALIS (APPLES) | PYRICULARIA ORYZAE (RICE) | CERCOSPORA ARACHIDICOLA (PEANUT) | PLASMOPARA VITICOLA (VINES) |
| 1 | 4 | 4 | 4 | 2 | 3 | 3 |
| 177 | 0 | 4 | 3 | 0 | 0 | 0 |

We claim:

1. A compound of the formula:

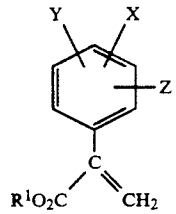

wherein $R^1$ is methyl; Y and Z are both hydrogen; and X is ortho to the $R^1O_2CC{=}CH_2$ group and is optionally substituted alkyl, optionally substituted alkenyl, optionally substituted alkynyl, alkoxy, haloalkoxy or optionally substituted arylalkoxy, with the proviso that X is not $CH_3O-$.

* * * * *

UNITED STATES PATENT AND TRADEMARK OFFICE
CERTIFICATE OF CORRECTION

PATENT NO. : 5,286,894

DATED : February 15, 1994

INVENTOR(S) : BUSHELL, Michael J. et al.

It is certified that error appears in the above-identified patent and that said Letters Patent is hereby corrected as shown below:

On title page, item

"[75] Inventors: Michael J. Bushnell; Kevin Beautement, both of Wokingham; John M. Clough, High Wycombe; Vivienne M. Anthony, Upminster; Paul deFraine, Wokingham, Christopher Godfrey, Bracknell, all of England" should read --[75] Inventors: Michael J. Bushell; Kevin Beautement, both of Wokingham; John M. Clough, High Wycombe; Vivienne M. Anthony, Upminster; Paul deFraine, Wokingham; Christopher Godfrey, Bracknell, all of England--.

Signed and Sealed this

Twenty-fifth Day of April, 1995

Attest:

BRUCE LEHMAN

Attesting Officer     Commissioner of Patents and Trademarks